US009844567B2

(12) United States Patent
Keyser et al.

(10) Patent No.: US 9,844,567 B2
(45) Date of Patent: Dec. 19, 2017

(54) MICROPOROUS ZIRCONIUM SILICATE FOR THE TREATMENT OF HYPERKALEMIA

(71) Applicant: ZS Pharma, Inc., Coppell, TX (US)

(72) Inventors: Donald Jeffrey Keyser, Southlake, TX (US); Alvaro F. Guillem, Lantana, TX (US)

(73) Assignee: ZS PHARMA, INC., Coppell, TX (US)

( * ) Notice: Subject to any disclaimer, the term of this patent is extended or adjusted under 35 U.S.C. 154(b) by 379 days.

(21) Appl. No.: 14/321,659

(22) Filed: Jul. 1, 2014

(65) Prior Publication Data
US 2014/0377359 A1  Dec. 25, 2014

Related U.S. Application Data

(63) Continuation of application No. 13/371,080, filed on Feb. 11, 2012, now Pat. No. 8,802,152.
(Continued)

(51) Int. Cl.
*A61K 33/24* (2006.01)
*C01B 39/00* (2006.01)
(Continued)

(52) U.S. Cl.
CPC ............... *A61K 33/24* (2013.01); *A61K 9/14* (2013.01); *A61K 9/143* (2013.01); *A61K 33/00* (2013.01); *A61K 45/06* (2013.01); *B01J 19/006* (2013.01); *B01J 19/0013* (2013.01); *B01J 19/0066* (2013.01); *B01J 19/18* (2013.01);
(Continued)

(58) Field of Classification Search
CPC .......... A61K 33/00; A61K 33/24; A61K 9/14; A61K 9/143; B01J 39/02; B01J 39/14; C01B 33/20; C01B 39/00; C01B 39/02; C01P 2004/52; C01P 2004/61
See application file for complete search history.

(56) References Cited

U.S. PATENT DOCUMENTS

| 3,329,480 A | 7/1967 | Young |
| 3,947,279 A | 3/1976 | Hudecek |

(Continued)

FOREIGN PATENT DOCUMENTS

| CN | 101426477 | 2/2007 |
| EP | 0384728 | 8/1990 |

(Continued)

OTHER PUBLICATIONS

International Preliminary Report on Patentability and Written Opinion of PCT/US2013/050071 dated Dec. 9, 2013.
(Continued)

*Primary Examiner* — Kortney L. Klinkel
(74) *Attorney, Agent, or Firm* — Arent Fox LLP

(57) ABSTRACT

The present invention relates to novel microporous zirconium silicate compositions that are formulated to remove toxins, e.g. potassium ions, from the gastrointestinal tract at an elevated rate without causing undesirable side effects. The preferred formulations are designed avoid increase in pH of urine in patients and/or avoid potential entry of particles into the bloodstream of the patient. Also disclosed is a method for preparing high purity crystals of UZSi-9 exhibiting an enhanced level of potassium exchange capacity. These compositions are particularly useful in the therapeutic treatment of hyperkalemia.

22 Claims, 18 Drawing Sheets

Red = ZrO3 (oct), Yellow = SiO2 (tet), Cations not shown

Related U.S. Application Data

(60) Provisional application No. 61/441,893, filed on Feb. 11, 2011.

(51) Int. Cl.

| | | |
|---|---|---|
| *A61K 45/06* | (2006.01) | |
| *A61K 9/14* | (2006.01) | |
| *C01B 39/02* | (2006.01) | |
| *B01J 39/14* | (2006.01) | |
| *B01J 39/02* | (2006.01) | |
| *B01J 19/18* | (2006.01) | |
| *A61K 33/00* | (2006.01) | |
| *B01J 19/00* | (2006.01) | |
| *C07F 7/02* | (2006.01) | |
| *C01B 33/20* | (2006.01) | |
| *C01B 39/46* | (2006.01) | |

(52) U.S. Cl.
CPC ............. *B01J 39/02* (2013.01); *B01J 39/14* (2013.01); *C01B 33/20* (2013.01); *C01B 39/00* (2013.01); *C01B 39/02* (2013.01); *C01B 39/46* (2013.01); *C07F 7/025* (2013.01); *B01J 2219/00063* (2013.01); *B01J 2219/00094* (2013.01); *B01J 2219/00768* (2013.01); *C01P 2002/72* (2013.01); *C01P 2002/82* (2013.01); *C01P 2004/52* (2013.01); *C01P 2004/61* (2013.01); *Y10T 428/2982* (2015.01)

(56) References Cited

U.S. PATENT DOCUMENTS

| | | |
|---|---|---|
| 4,581,141 A | 4/1986 | Ash |
| 4,943,545 A | 7/1990 | Chang |
| 5,015,453 A | 5/1991 | Chapman |
| 5,338,527 A | 8/1994 | Lambert |
| 5,518,707 A | 5/1996 | Bedard et al. |
| 5,624,652 A | 4/1997 | Aldcroft et al. |
| 5,888,472 A | 3/1999 | Bem et al. |
| 5,891,417 A | 4/1999 | Bem et al. |
| 5,910,299 A | 6/1999 | Carluccio et al. |
| 6,007,790 A | 12/1999 | Bedard et al. |
| 6,099,737 A | 8/2000 | Sherman et al. |
| 6,146,613 A | 11/2000 | Anglerot et al. |
| 6,159,505 A | 12/2000 | Piper |
| 6,332,985 B1 | 12/2001 | Sherman et al. |
| 6,379,641 B1 | 4/2002 | Bedard et al. |
| 6,579,460 B1 | 6/2003 | Willis et al. |
| 6,596,254 B1 | 7/2003 | Nenoff et al. |
| 6,689,335 B1 | 2/2004 | Bringley et al. |
| 6,814,871 B1 | 11/2004 | Bem et al. |
| 7,297,319 B2 | 11/2007 | Vitale-Rojas et al. |
| 7,488,495 B2 | 2/2009 | Charmot et al. |
| 7,566,432 B2 | 7/2009 | Wong |
| 7,854,924 B2 | 12/2010 | Alpern et al. |
| 7,967,984 B2 | 6/2011 | Midorikawa et al. |
| 8,093,350 B2 | 1/2012 | Jung et al. |
| 8,192,758 B2 | 6/2012 | Charmot et al. |
| 8,282,960 B2 | 10/2012 | Charmot et al. |
| 8,431,502 B2 | 4/2013 | Dejneka et al. |
| 8,802,152 B2 | 8/2014 | Keyser et al. |
| 8,808,750 B2 | 8/2014 | Keyser et al. |
| 8,877,255 B2 | 11/2014 | Keyser et al. |
| 2004/0105895 A1 | 6/2004 | Ash |
| 2005/0220752 A1 | 10/2005 | Charmot et al. |
| 2007/0128424 A1 | 6/2007 | Omari et al. |
| 2007/0202180 A1 | 8/2007 | Liversidge et al. |
| 2007/0269499 A1 | 11/2007 | Hen et al. |
| 2008/0241092 A1 | 10/2008 | Charmot et al. |
| 2009/0155370 A1 | 6/2009 | Cope et al. |
| 2009/0186093 A1 | 7/2009 | Liu et al. |
| 2009/0263478 A1 | 10/2009 | Arnold et al. |
| 2010/0104527 A1 | 4/2010 | Mansky et al. |
| 2010/0322847 A1 | 12/2010 | Xiao et al. |
| 2011/0097401 A1 | 4/2011 | Phillips et al. |
| 2012/0070468 A1 | 3/2012 | Bedard et al. |
| 2012/0213847 A1 | 8/2012 | Keyser et al. |
| 2012/0259141 A1 | 10/2012 | Yilmaz et al. |
| 2012/0289931 A1 | 11/2012 | Robinson et al. |
| 2013/0123096 A1 | 5/2013 | Xiao et al. |
| 2013/0129611 A1 | 5/2013 | Maurer et al. |
| 2013/0202524 A1 | 8/2013 | Maurer et al. |
| 2013/0259949 A1 | 10/2013 | Cope et al. |
| 2013/0296159 A1 | 11/2013 | Feyen et al. |
| 2014/0044804 A1 | 2/2014 | Cope et al. |

FOREIGN PATENT DOCUMENTS

| | | |
|---|---|---|
| EP | 0451958 | 10/1991 |
| EP | 0832897 A2 | 4/1998 |
| EP | 1038580 | 3/1999 |
| EP | 0982785 | 3/2000 |
| ES | 2304890 | 10/2008 |
| GB | 2038301 | 7/1980 |
| WO | 02062356 | 8/2002 |
| WO | 2005053650 A1 | 6/2005 |
| WO | 2007100466 | 11/2007 |
| WO | 2010022381 | 2/2010 |
| WO | 2012109590 A2 | 8/2012 |

OTHER PUBLICATIONS

International Search Report and Written Opinion of PCT/US2014/064542 dated Jan. 27, 2015.
International Search Report and Written Opinion of PCT/US2014/064548 dated Jan. 27, 2015.
International Search Report and Written Opinion of PCT/US2014/69524 dated Mar. 3, 2015.
Timmer et al., Journal of the American Society of Nephrology (1999) vol. 10, pp. 666-674.
Stephen R. Ash, "Sorbents in Treatment of Uremia: A Short History and a Great Future," Seminars in Dialysis, vol. 22, No. 6 (Nov.-Dec. 2009), pp. 615-622.
Stephen R. Ash, Cation Exchangers as Oral Sorbents for Ammonium and Potassium: PSS, ZP and ZS (Zirconium Silicate), Clarian Arnett Health, Wellbound and HemoCleanse Inc., Lafayette, IN, (2007), ASAIO Innovation Conference, Chicago (25 pages).
David S. Bem et al., "Synthesis and Characterization of a New Family of Microporous Zirconium Silicates," (1999), Materials Research Society, Symposium Procedures, vol. 549, pp. 73-78.
Bortun et al., Chem. Mater. (1997) vol. 9, No. 8, pp. 1854-1864.
Rich Braun et al., "Ammonium Removal With a Novel Zirconium Silicate," Presentation, (2001), ASAIO Conference (16 pages).
Chukanov et al., Russian Journal of Physical Chemistry B (2011) vol. 5, No. 2, pp. 278-283.
Chukanov et al., Russian Journal of Physical Chemistry B (2011) vol. 5, No. 2, pp. 284-289.
Chukanov et al., Minerals as Advanced Materials II (2012) pp. 167-179 (S.V. Krivovichev (ed)).
Clearfield et al., Journal of Molecular Structure (1998) vol. 470, pp. 207-213.
Dunn et al., American Mineralogist (1977) vol. 62, pp. 416-420.
Ferreira et al., Chem. Mater. (2001) vol. 13, pp. 355-363.
Ferreira et al., Inorganica Chimica Acta (2003) vol. 356, pp. 19-26.
Ferreira et al., Journal of Solid State Chemistry (2010) vol. 183, pp. 3067-3072.
Fewox et al., J. Phys. Chem. A (2008) vol. 112, pp. 2589-2597.
Fundamental of Physics © 1997 John Wiley & Sons, Inc., USA, pp. 947-949, section 37-9 X-Ray Diffraction.
Henderson, Lee W., Seminars in Dialysis (2012) vol. 25, No. 3, pp. 320-325.
International Search Report and Written Opinion of PCT/US2012/024727 dated Aug. 7, 2012.
International Search Report and Written Opinion of PCT/US2013/066207 dated Feb. 14, 2014.
International Search Report and Written Opinion of PCT/US2013/045219 dated Nov. 8, 2013.
Lopes et al., Quim. Nova. (2008) vol. 31, No. 2, pp. 321-325.

(56) References Cited

OTHER PUBLICATIONS

Navascues et al., Desalination (2006) vol. 199, pp. 368-370.
Navascues et al., Chemical Engineering and Processing (2008) vol. 47, pp. 1139-1149.
Pekov et al., Cryst. Report (2010) vol. 55, No. 6, pp. 1031-1040.
Pertierra et al., Inorganic Chemistry Comm. (2002) vol. 5, pp. 824-828.
Poojary et al., Inorg. Chem. (1997) vol. 36, pp. 3072-3079.
Rocha et al., Chem. Comm. (1998) 1269-1270.
Yong-Nan et al., Chem. Res. Chinese U. (2002) vol. 18, No. 4, pp. 380-384.
ZS-9 Particle Size Distribution Analysis Report (4 pages), Nov. 4, 2009.
ZS Pharma Products website from Sep. 9, 2010 (http://web.archive.org/web/20100906160415/http://zspharma.com/products, accessed Mar. 28, 2014 via archive.org).
ZS Pharma Welcome website Sep. 6, 2010 (http://web.archive.org/web/20100906213849/http://zspharma.com/index.
php?format=feed&type=atom, accessed Mar. 28, 2014 via archive.org) containing a comment from Dan Olson from Jan. 9, 2010.
International Search Report and Written Opinion of PCT/US2014/032815 dated Nov. 6, 2014.
Roswell et al., "Metal-organic Frameworks: A New Class of Porous Materials," Microporous and Mesoporous Materials (2004) vol. 73, pp. 3-14.
Baussy et al., "Minéralogie expèrimentale dans le systéme $ZrO_2$—$SiO_2$—$Na_2O$—$H_2O$. Corrèlations pètrogénètiques," Bull. Soc. fr. Minéral Cristallogr., 1974, vol. 97, pp. 433-444.

Red = ZrO3 (oct), Yellow = SiO2 (tet), Cations not shown

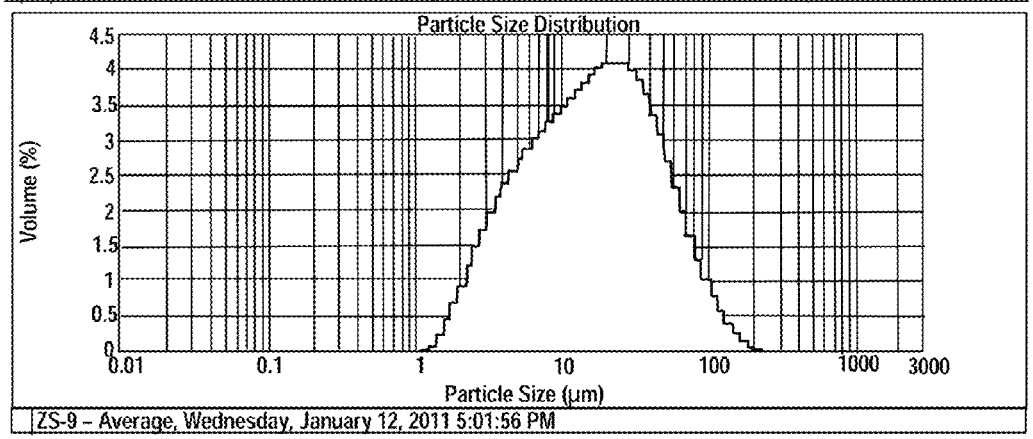
Fig. 2 (ZS-9 lot 5332-04310-A)

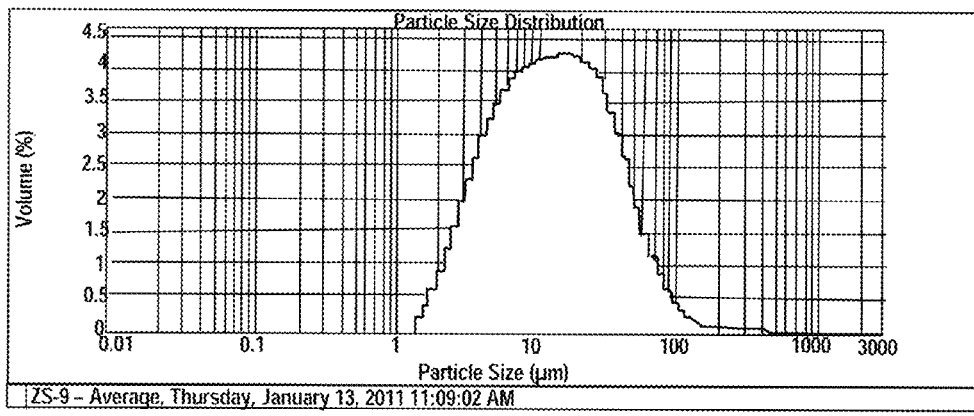
Fig. 3 (ZS-9 lot 5332-04310-A)

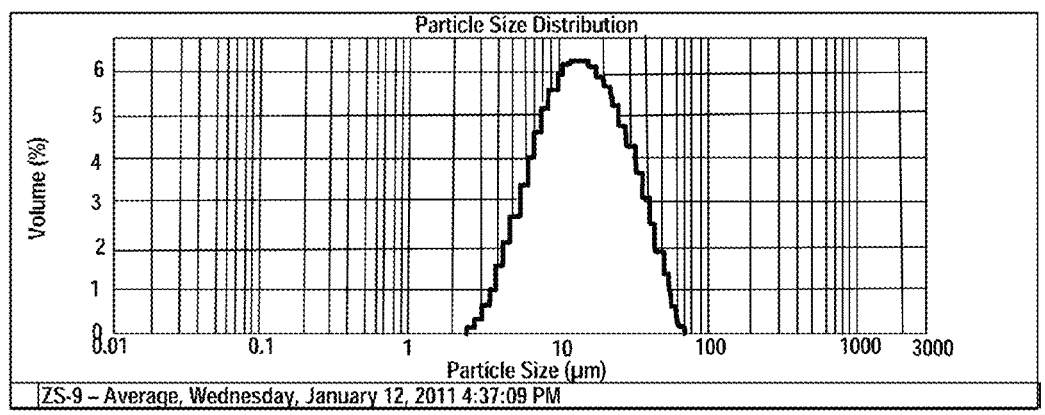
Fig. 4 (ZS-9 preclinical lot))

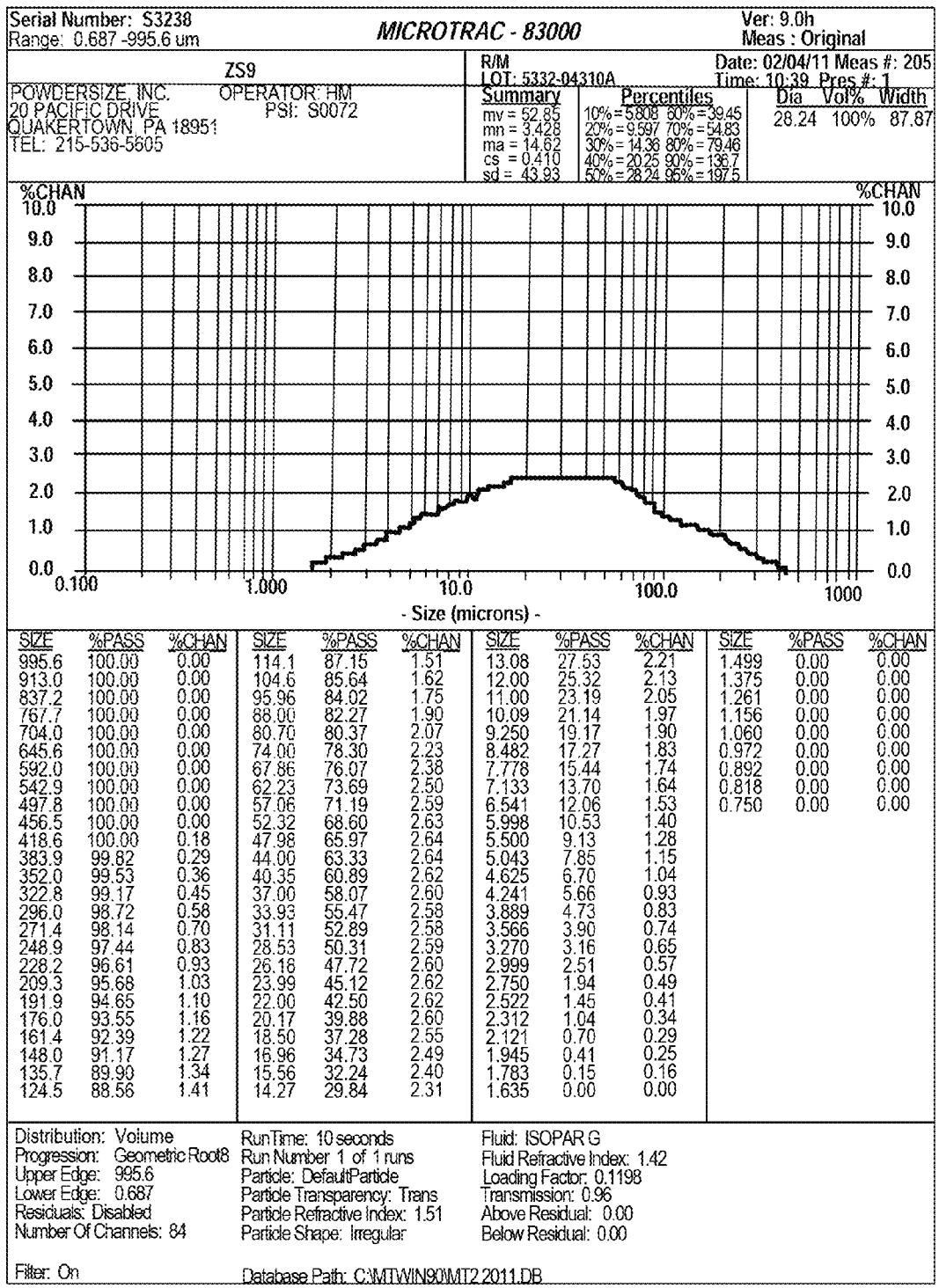
Fig. 5 (lot 5332-04310A w/o screening)

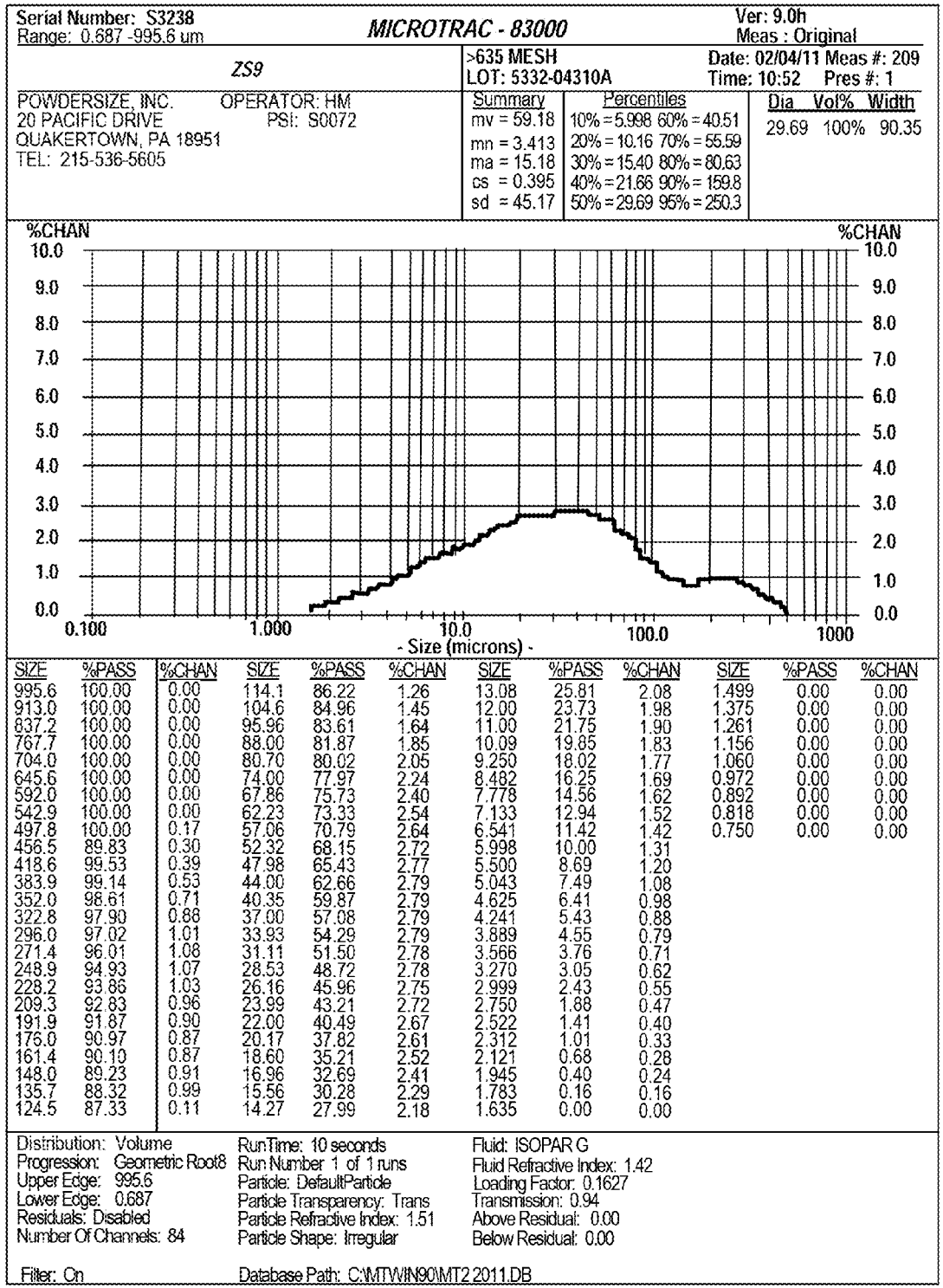
Fig. 6 (lot 5332-04310A 635 mesh)

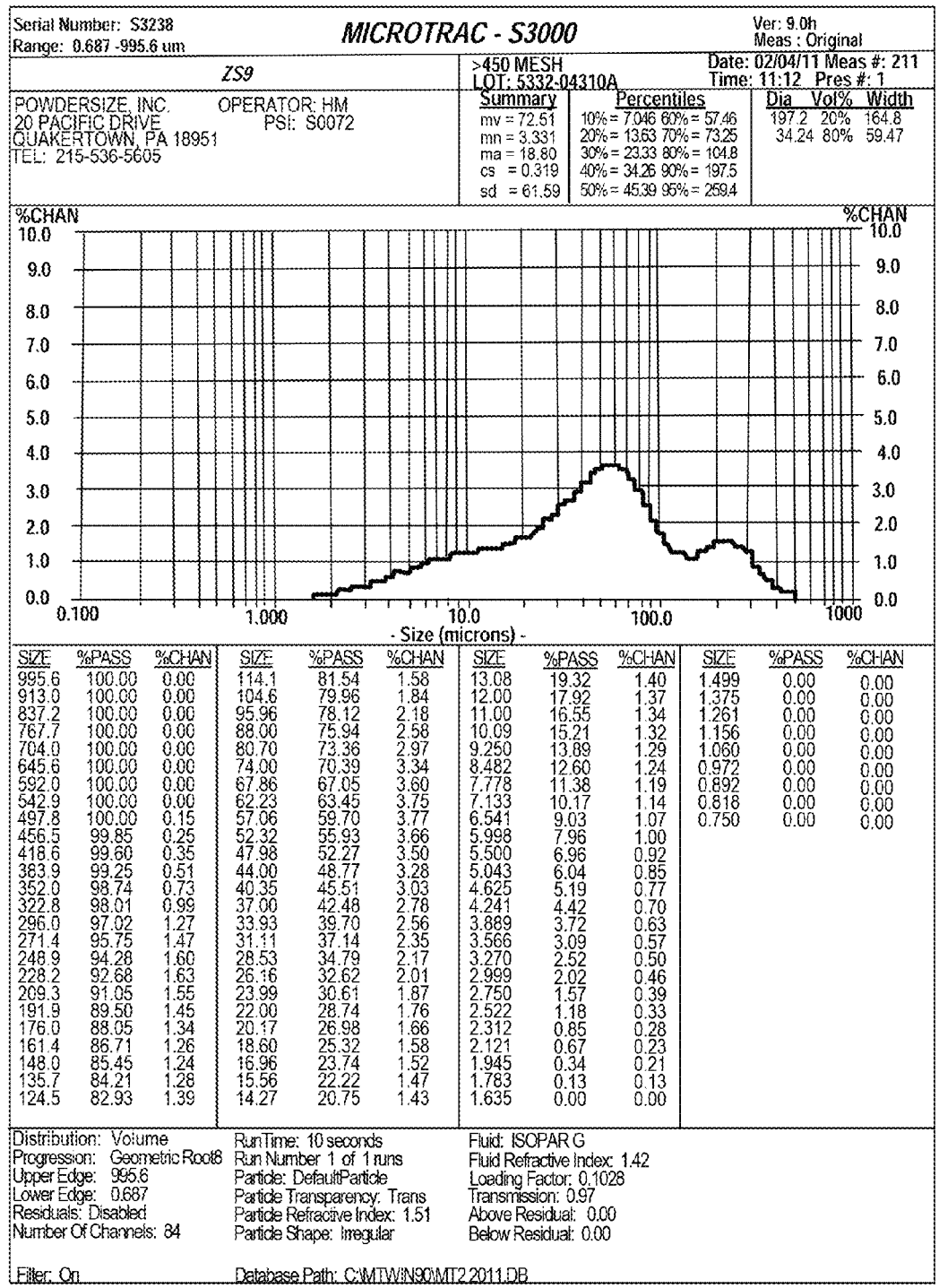
Fig. 7 (lot 5332-04310A 450 mesh)

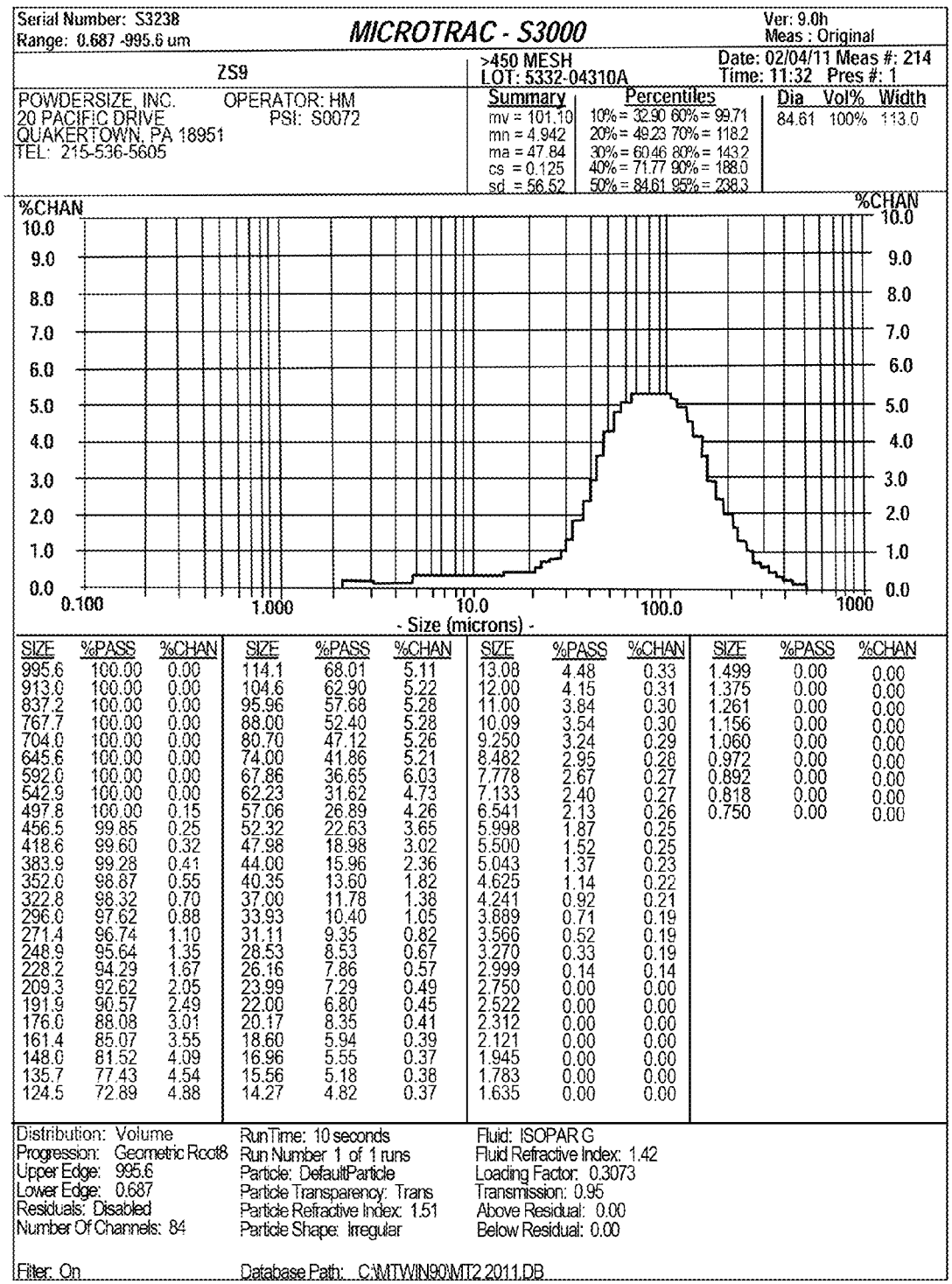
Fig. 8 (lot 5332-04310A 325 mesh)

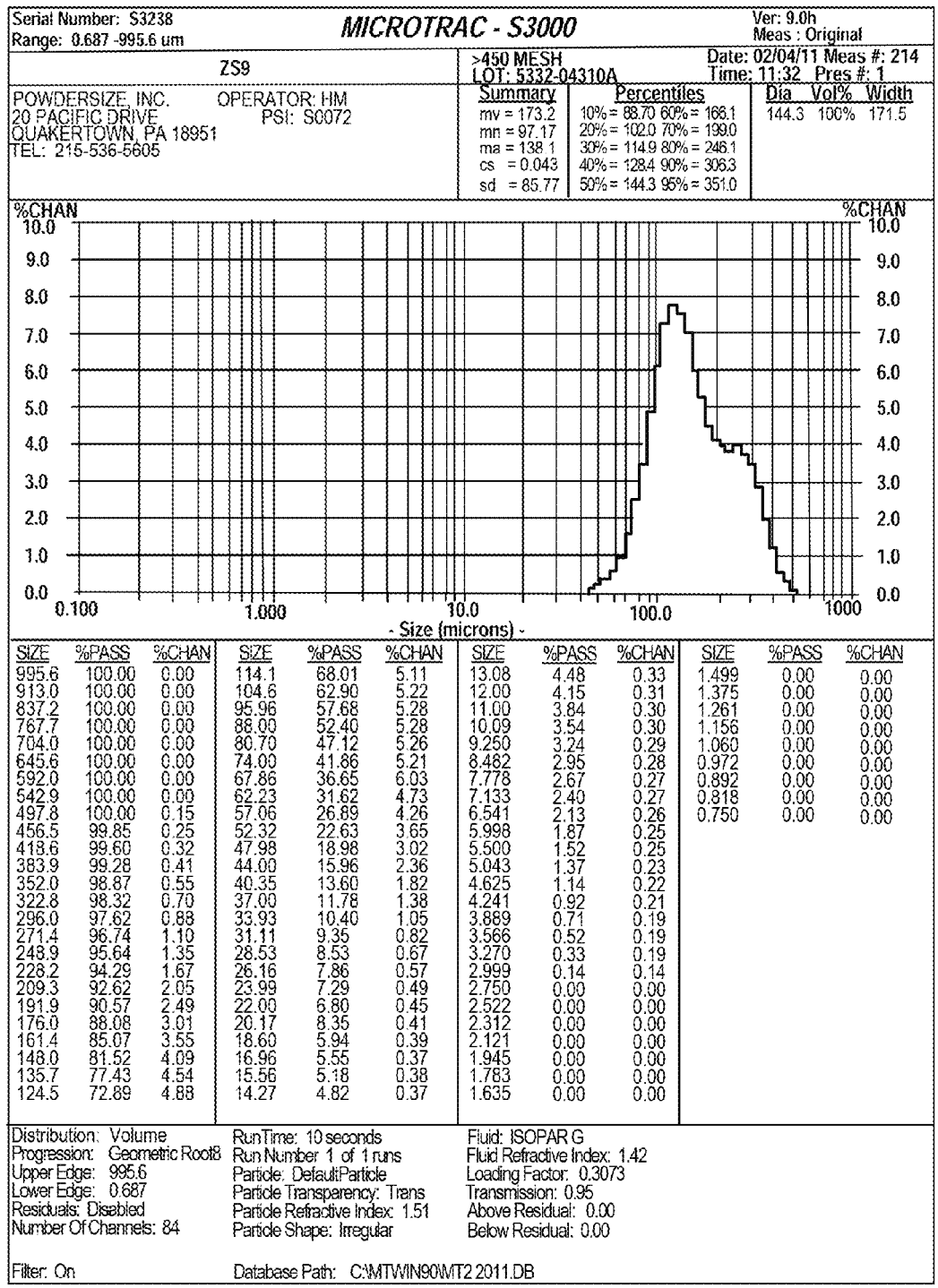
Fig. 9 (lot 5332-04310A 230 mesh)

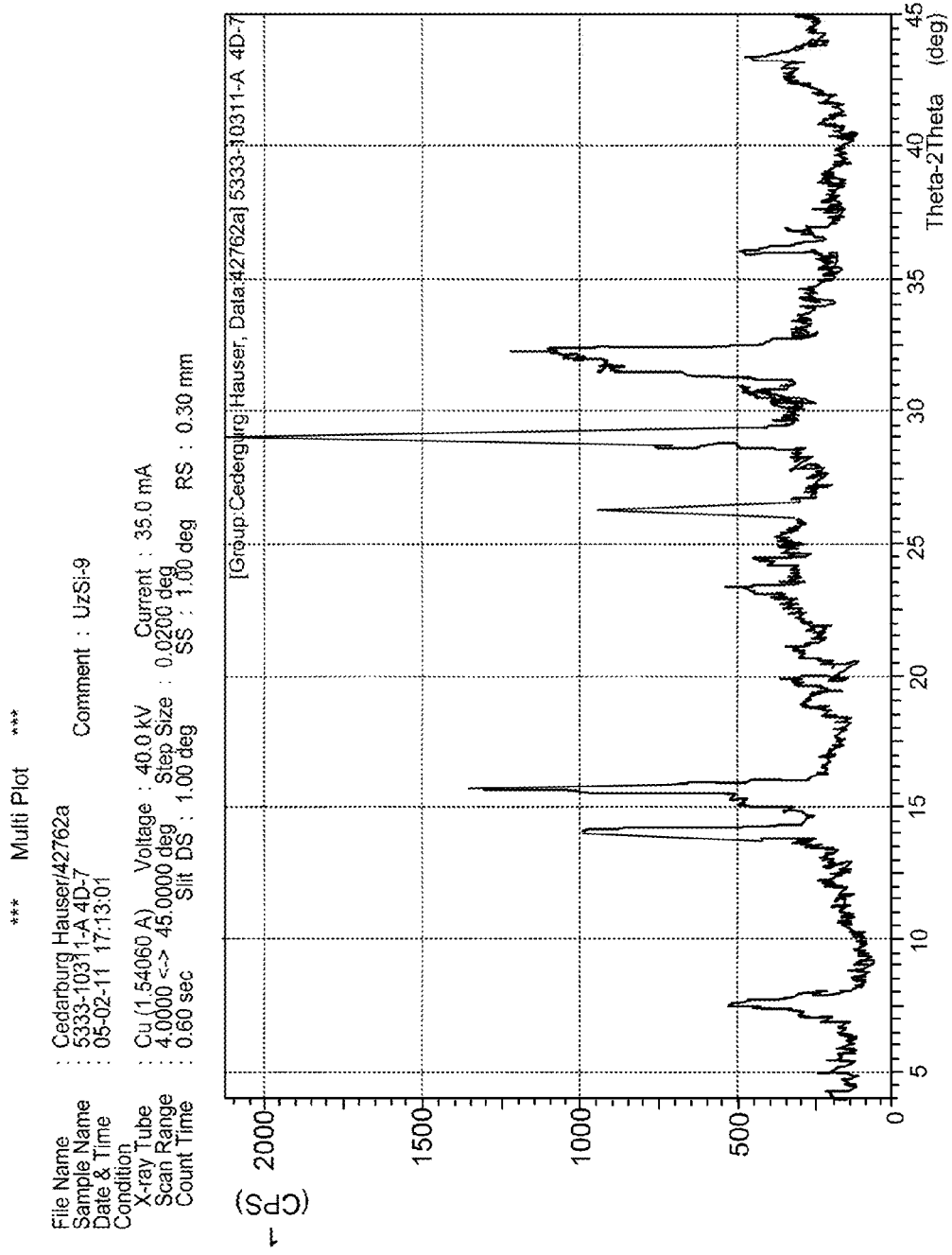
Fig. 10: XRD plot for ZS-9 prepared in accordance with Example 12.

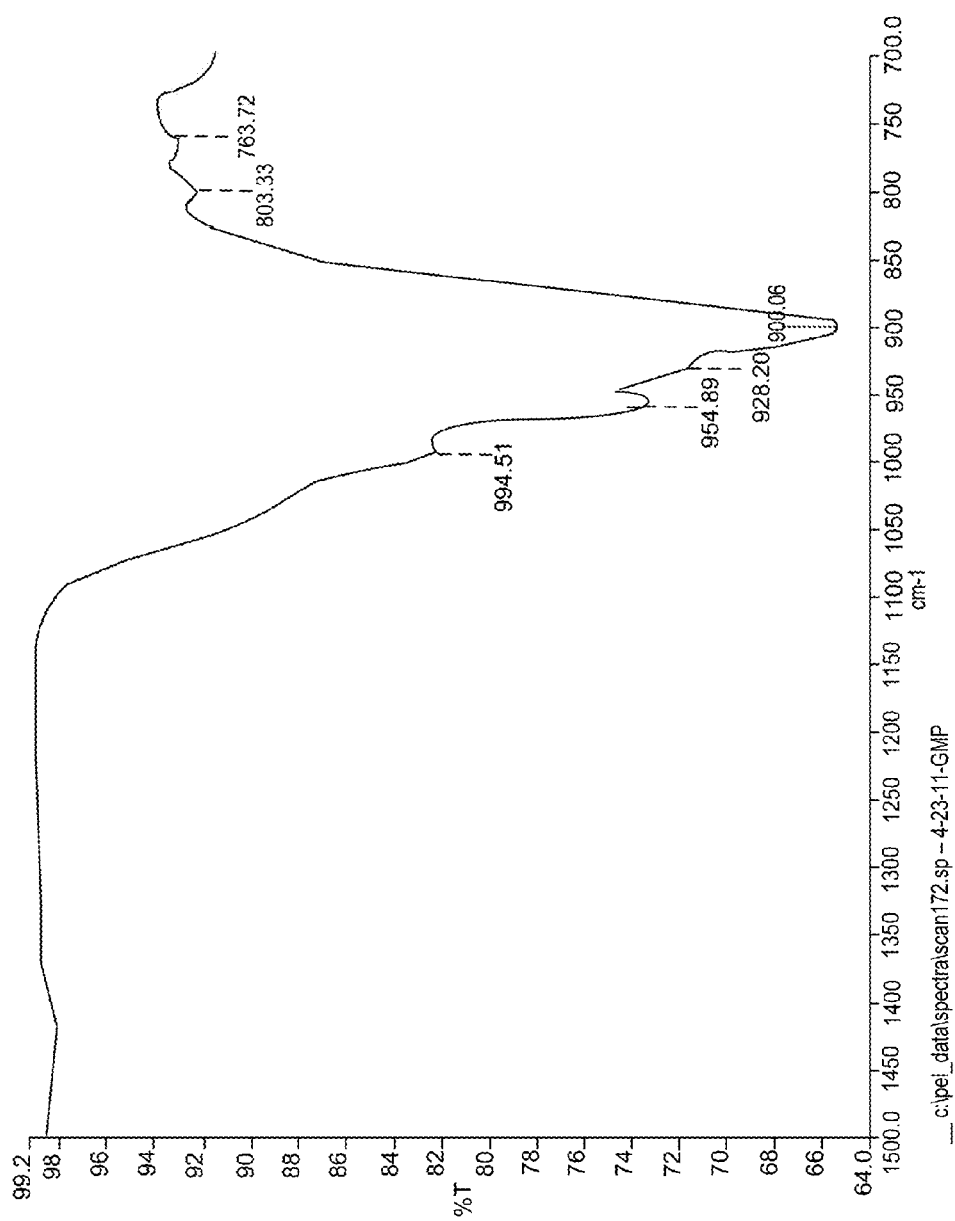
Fig. 11: FTIR plot for ZS-9 prepared in accordance with Example 12.

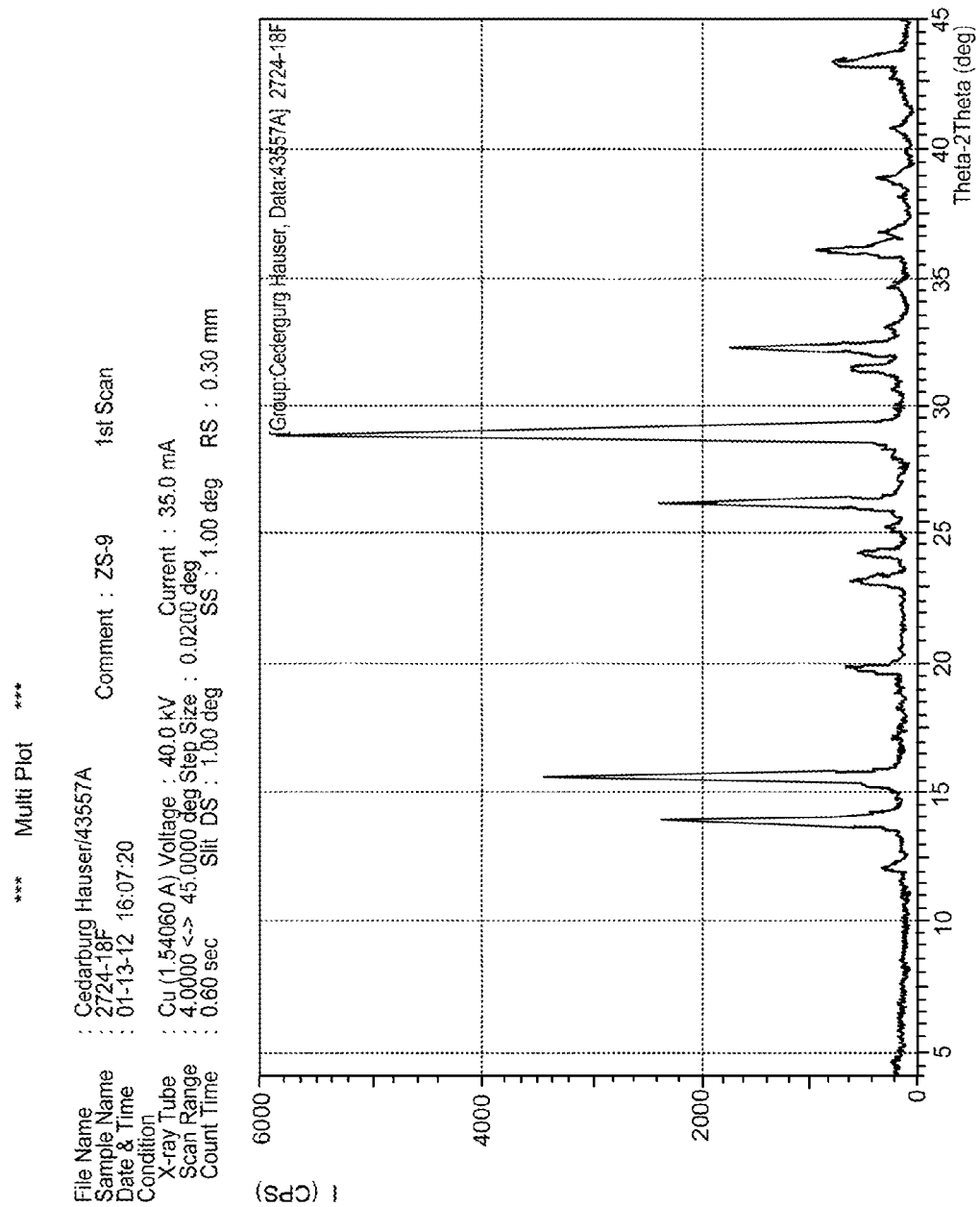
Fig. 12: XRD plot for ZS-9 prepared in accordance with Example 13.

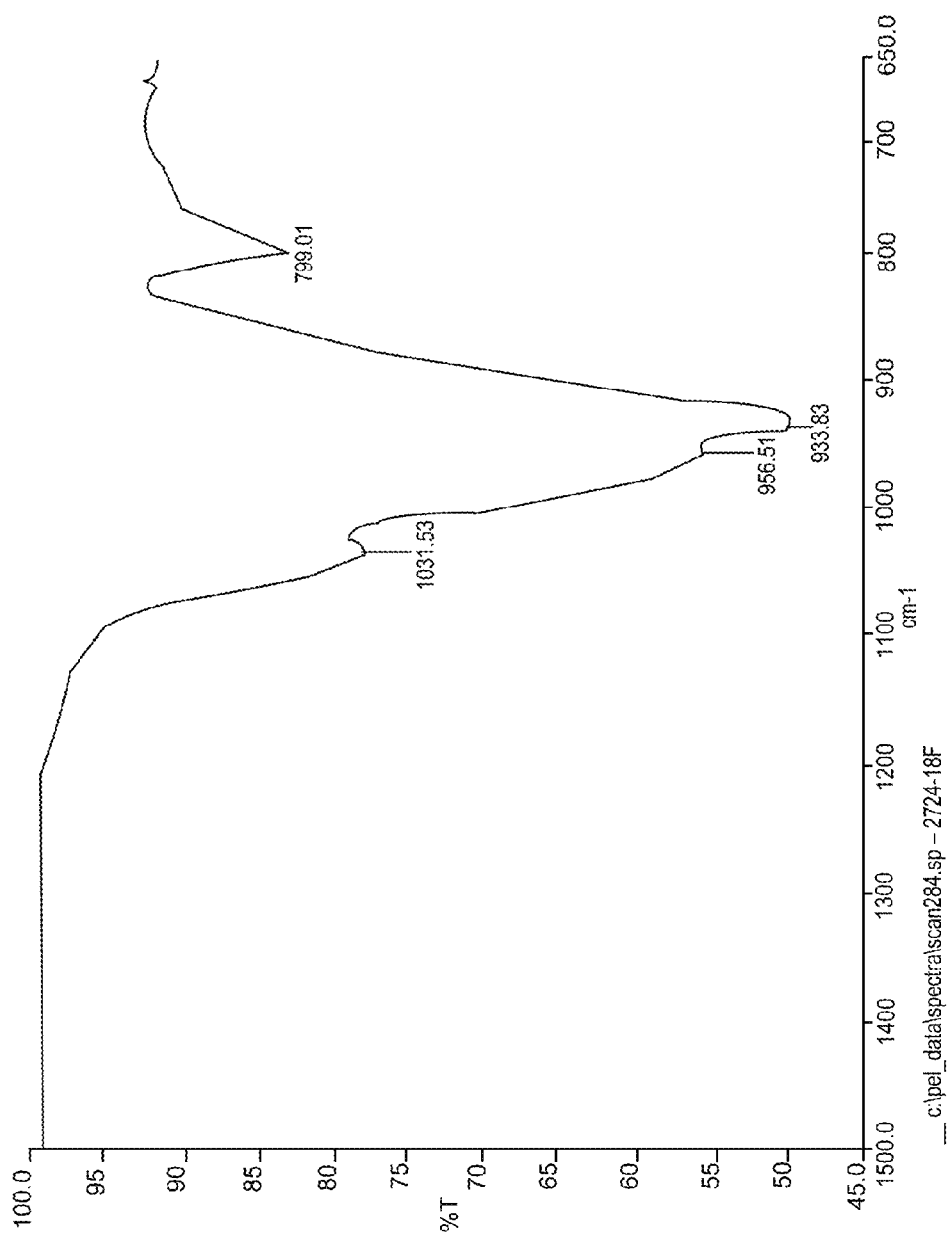
Fig. 13: FTIR plot for ZS-9 prepared in accordance with Example 13.

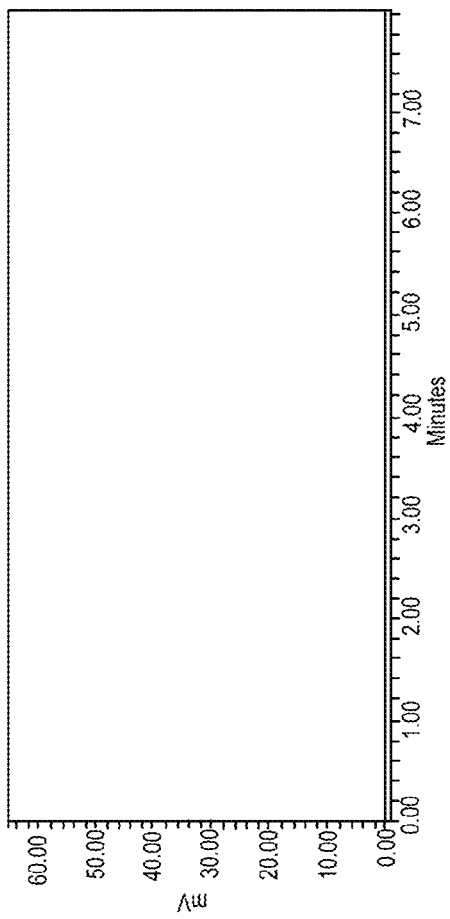
Fig. 14: Example of the Blank Solution Chromatogram
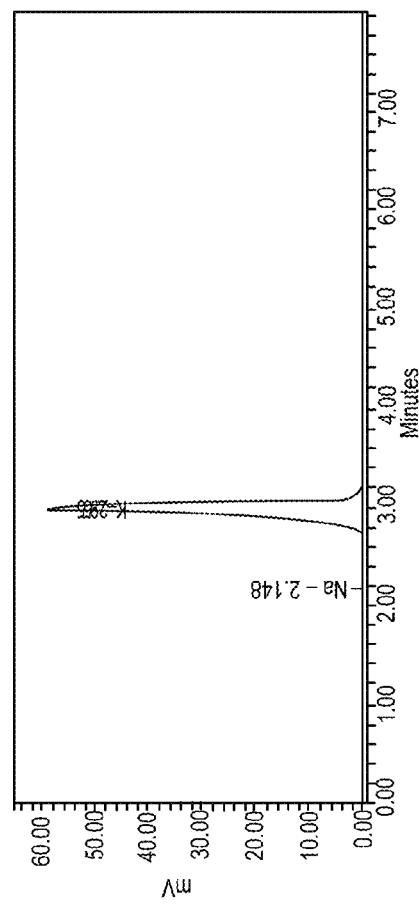
Fig. 15: Example of the Assay Standard Solution Chromatogram.

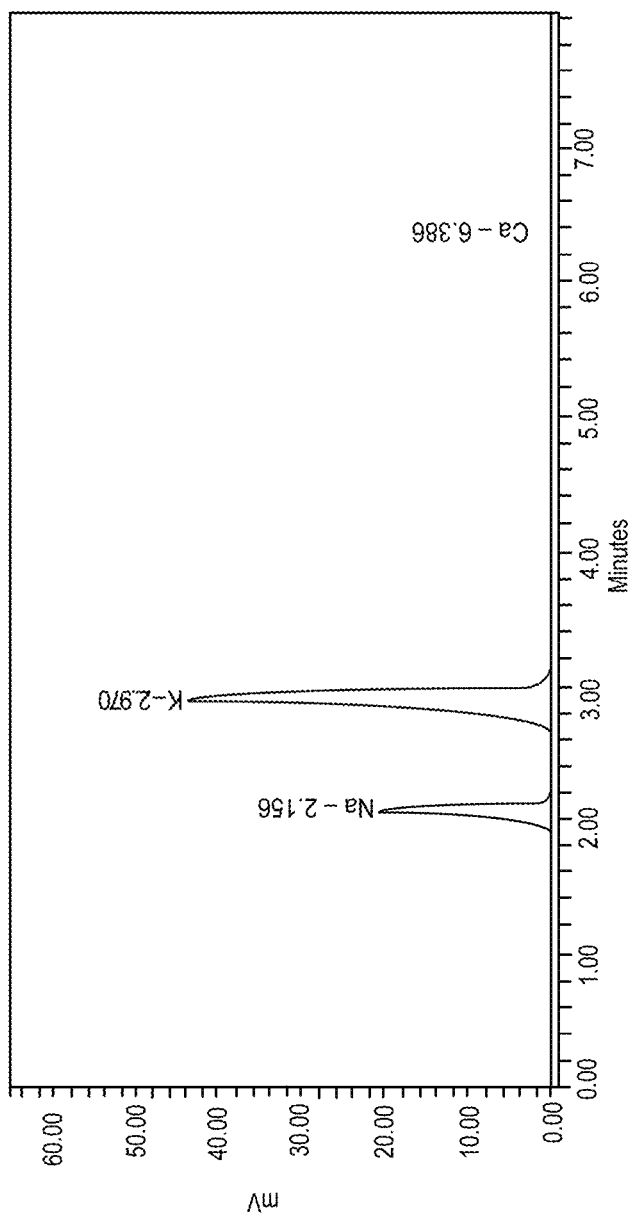
Fig. 16: Exemplary Sample Chromatogram.

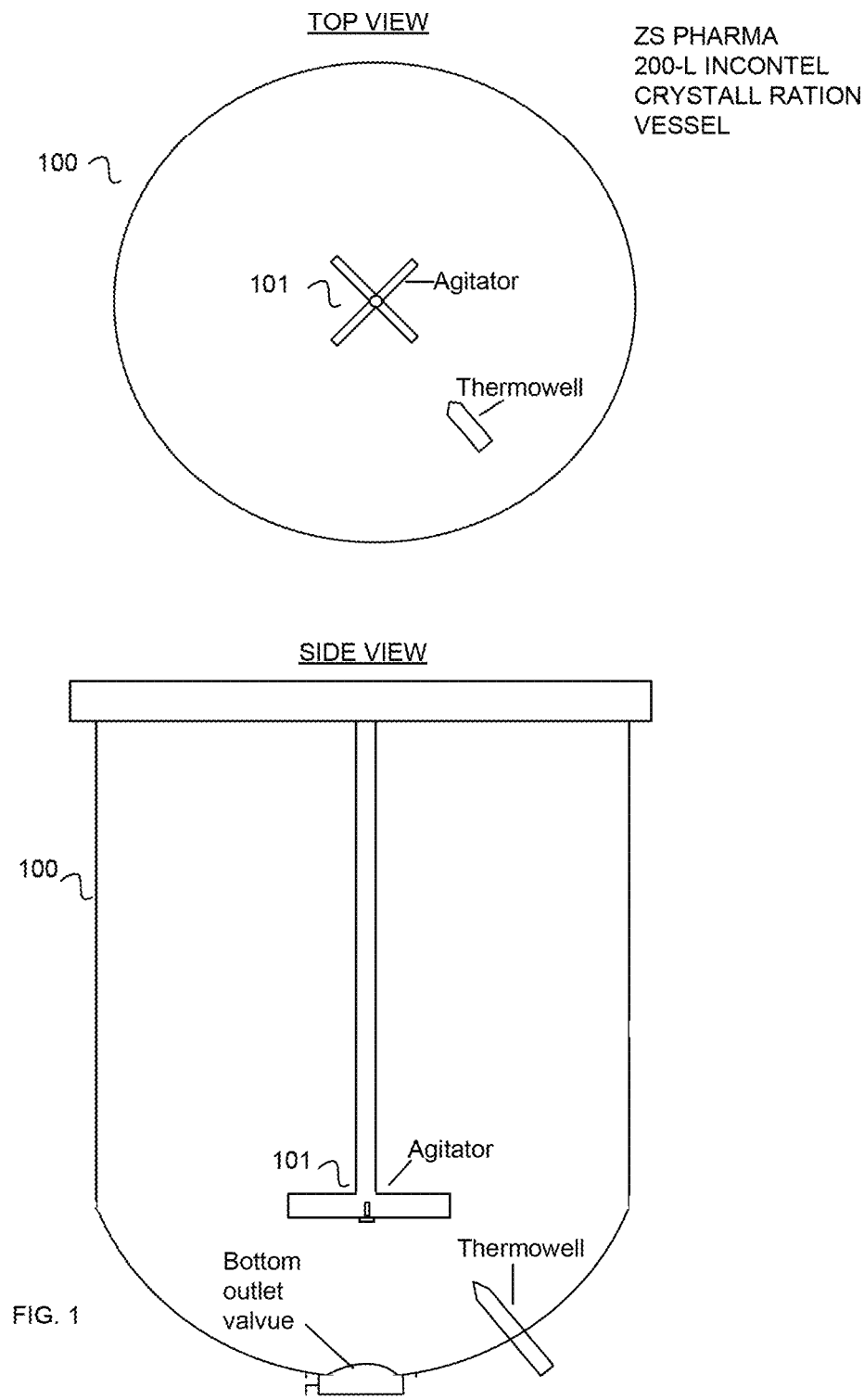
Fig. 17: 200-L reaction vessel with standard agitator arrangement.

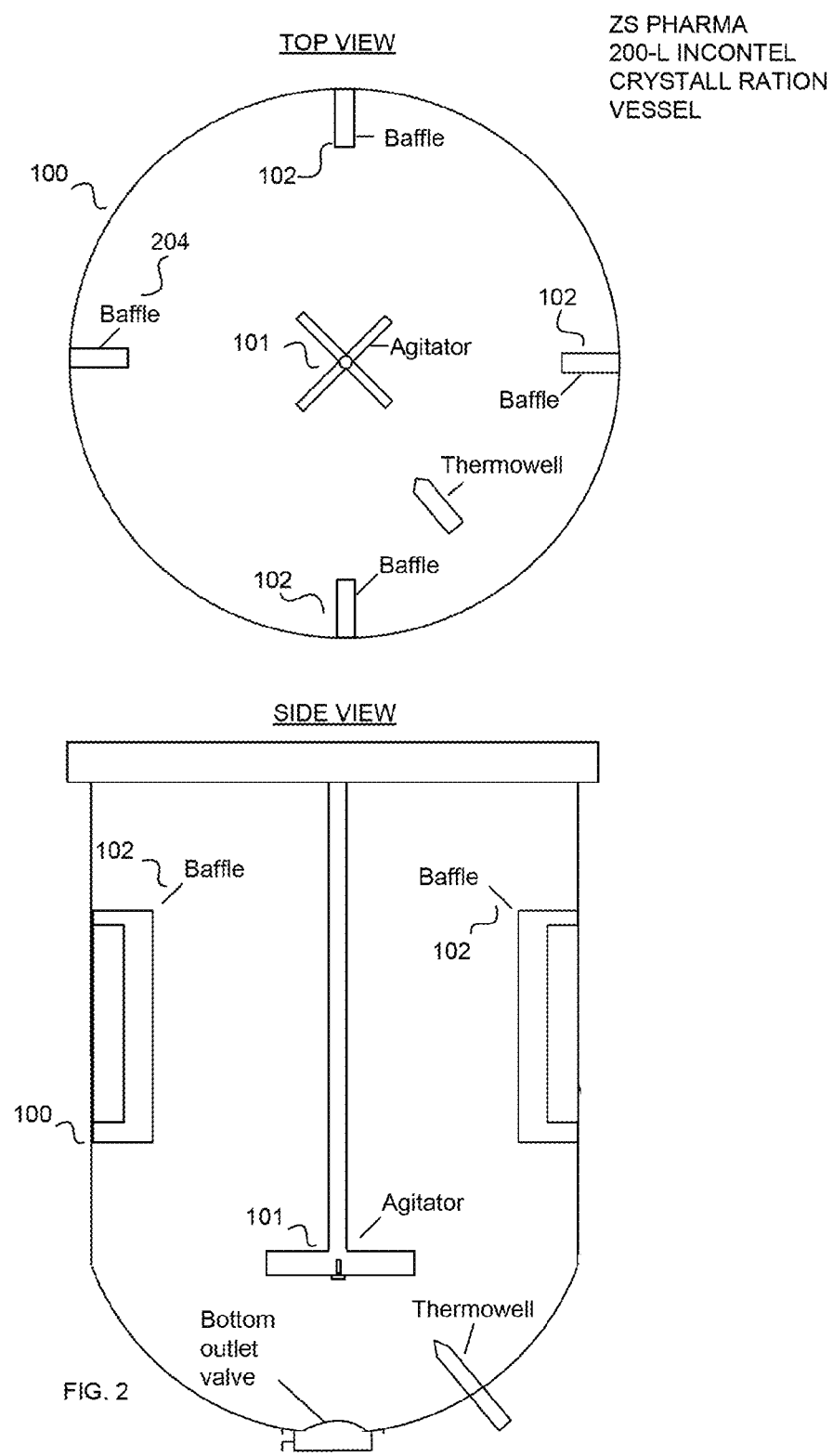
Fig. 18: 200-L reaction vessel with baffles for production of enhanced ZS-9

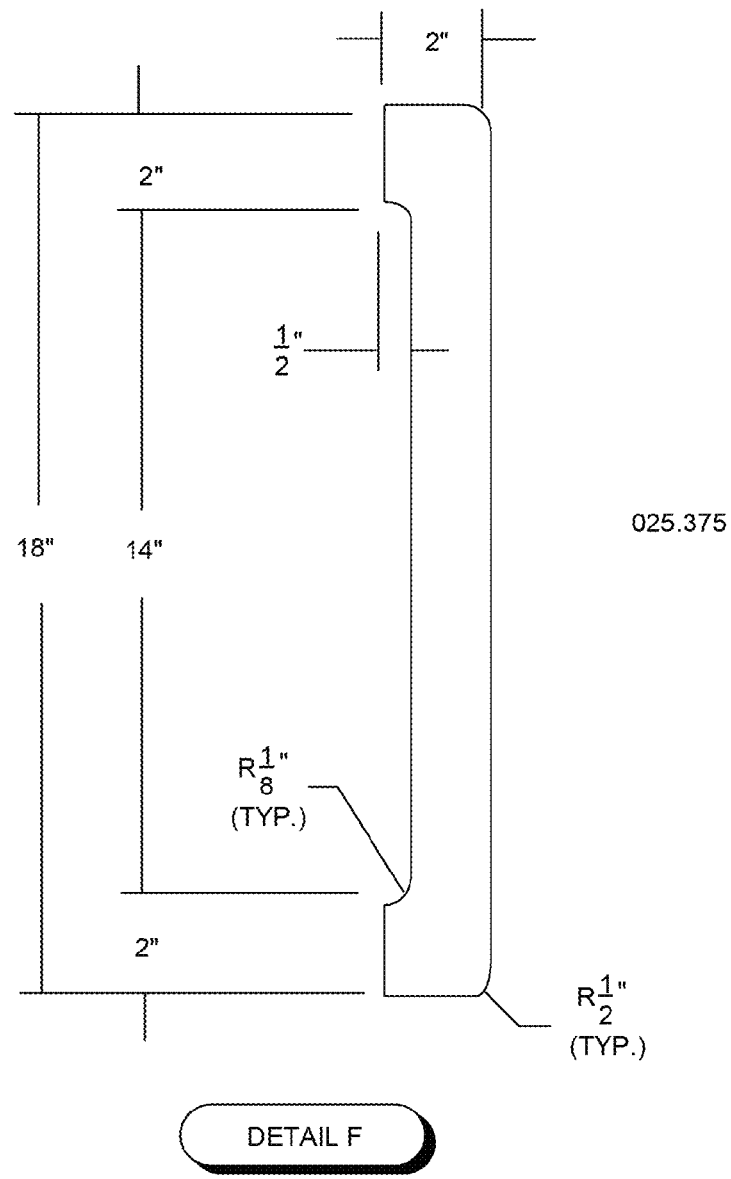
Fig. 19: Detail of baffle design for 200-L reaction vessel for production of enhanced ZS-9

MICROPOROUS ZIRCONIUM SILICATE FOR THE TREATMENT OF HYPERKALEMIA

CROSS-REFERENCE TO RELATED APPLICATIONS

This application is a continuation of U.S. patent application Ser. No. 13/371,080, filed Feb. 10, 2012, which claims priority to U.S. Provisional Patent Application No. 61/441,893, filed Feb. 11, 2011, the contents of each are hereby incorporated by reference in their entireties.

BACKGROUND OF THE INVENTION (i) Field of the Invention

The present invention relates to novel microporous zirconium silicate compositions that are formulated to remove toxins, e.g., potassium ions or ammonium ions, from the gastrointestinal tract at an elevated rate without causing undesirable side effects. The preferred formulations are designed to avoid potential entry of particles into the bloodstream and potential increase in pH of urine in patients. These compositions are particularly useful in the therapeutic treatment of hyperkalemia. Also disclosed are microporous zirconium silicate compositions having enhanced purity and potassium exchange capacity (KEC), and methods and apparatus for making such microporous zirconium silicate compositions.

(i) Description of the Related Art

Acute hyperkalemia is a serious life threatening condition resulting from elevated serum potassium levels. Potassium is a ubiquitous ion, involved in numerous processes in the human body. It is the most abundant intracellular cation and is critically important for numerous physiological processes, including maintenance of cellular membrane potential, homeostasis of cell volume, and transmission of action potentials. Its main dietary sources are vegetables (tomatoes and potatoes), fruit (oranges, bananas) and meat. The normal potassium levels in plasma are between 3.5-5.0 mmol/l with the kidney being the main regulator of potassium levels. The renal elimination of potassium is passive (through the glomeruli) with active reabsorption in the proximal tubule and the ascending limb of the loop of Henle. There is active excretion of potassium in the distal tubules and the collecting duct, both of which processes are controlled by aldosterone.

Increased extracellular potassium levels result in depolarization of the membrane potential of cells. This depolarization opens some voltage-gated sodium channels, but not enough to generate an action potential. After a short period of time, the open sodium channels inactivate and become refractory, increasing the threshold to generate an action potential. This leads to impairment of the neuromuscular-, cardiac- and gastrointestinal organ systems, and this impairment is responsible for the symptoms seen with hyperkalemia. Of greatest concern is the effect on the cardiac system, where impairment of cardiac conduction can lead to fatal cardiac arrhythmias such as asystole or ventricular fibrillation. Because of the potential for fatal cardiac arrhythmias, hyperkalemia represents an acute metabolic emergency that must be immediately corrected.

Hyperkalemia may develop when there is excessive production of serum potassium (oral intake, tissue breakdown). Ineffective elimination, which is the most common cause of hyperkalemia, can be hormonal (as in aldosterone deficiency), pharmacologic (treatment with ACE-inhibitors or angiotensin-receptor blockers) or, more commonly, due to reduced kidney function or advanced cardiac failure. The most common cause of hyperkalemia is renal insufficiency, and there is a close correlation between degree of kidney failure and serum potassium (S—K) levels. In addition, a number of different commonly used drugs cause hyperkalemia, such as ACE-inhibitors, angiotensin receptor blockers, potassium-sparing diuretics (e.g. amiloride, spironolactone), NSAIDs (such as ibuprofen, naproxen, celecoxib), heparin and certain cytotoxic and/or antibiotic drugs (such as cyclosporin and trimethoprim). Finally, beta-receptor blocking agents, digoxin or succinylcholine are other well-known causes of hyperkalemia. In addition, advanced degrees of congestive heart disease, massive injuries, burns or intravascular hemolysis cause hyperkalemia, as can metabolic acidosis, most often as part of diabetic ketoacidosis.

Symptoms of hyperkalemia are somewhat non-specific and generally include malaise, palpitations and muscle weakness or signs of cardiac arrhythmias, such as palpitations, brady-tachycardia or dizziness/fainting. Often, however, the hyperkalemia is detected during routine screening blood tests for a medical disorder or after severe complications have developed, such as cardiac arrhythmias or sudden death. Diagnosis is obviously established by S—K measurements.

Treatment depends on the S—K levels. In milder cases (S—K between 5-6.5 mmol/l), acute treatment with a potassium binding resin (Kayexalate®), combined with dietary advice (low potassium diet) and possibly modification of drug treatment (if treated with drugs causing hyperkalemia) is the standard of care; if S—K is above 6.5 mmol/l or if arrhythmias are present, emergency lowering of potassium and close monitoring in a hospital setting is mandated. The following treatments are typically used:

Kayexalate®, a resin that binds potassium in the intestine and hence increases fecal excretion, thereby reducing S—K levels. However, as Kayexalate® has been shown to cause intestinal obstruction and potential rupture. Further, diarrhea needs to be simultaneously induced with treatment. These factors have reduced the palatability of treatment with Kayexalate®.

Insulin IV (+glucose to prevent hypoglycemia), which shifts potassium into the cells and away from the blood.

Calcium supplementation. Calcium does not lower S—K, but it decreases myocardial excitability and hence stabilizes the myocardium, reducing the risk for cardiac arrhythmias.

Bicarbonate. The bicarbonate ion will stimulate an exchange of K+ for Na+, thus leading to stimulation of the sodium-potassium ATPase.

Dialysis (in severe cases).

The only pharmacologic modality that actually increases elimination of potassium from the body is Kayexalate®; however, due to the need to induce diarrhea, Kayexalate® cannot be administered on a chronic basis, and even in the acute setting, the need to induce diarrhea, combined with only marginal efficacy and a foul smell and taste, reduces its usefulness.

The use of zirconium silicate or titanium silicate microporous ion exchangers to remove toxic cations and anions from blood or dialysate is described in U.S. Pat. Nos. 6,579,460, 6,099,737, and 6,332,985, each of which is incorporated herein in their entirety. Additional examples of microporous ion exchangers are found in U.S. Pat. Nos. 6,814,871, 5,891,417, and 5,888,472, each of which is incorporated herein in their entirety.

The inventors have found that known zirconium silicate compositions may exhibit undesirable effects when utilized in vivo for the removal of potassium in the treatment of hyperkalemia. Specifically, the administration of zirconium silicate molecular sieve compositions has been associated with an incidence of mixed leukocyte inflammation, minimal acute urinary bladder inflammation and the observation of unidentified crystals in the renal pelvis and urine in animal studies, as well as an increase in urine pH. Further, known zirconium silicate compositions have had issues with crystalline impurities and undesirably low cation exchange capacity.

The inventors have discovered novel zirconium silicate molecular sieves to address the problem associated with existing hyperkalemia treatments, and novel methods of treatment for hyperkalemia utilizing these novel compositions.

SUMMARY OF THE INVENTION

Zirconium silicate and zirconium germanate molecular sieves have a microporous structure composed of $ZrO_3$ octahedral units and at least one $SiO_2$ tetrahedral units and $GeO_2$ tetrahedral units. These molecular sieves have the empirical formula:

$$A_pM_xZr_{1-x}Si_nGe_yO_m \quad (I)$$

where A is an exchangeable cation selected from potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), "p" has a value from about 1 to about 20, "x" has a value from 0 to less than 1, "n" has a value from about 0 to about 12, "y" has a value from 0 to about 12, "m" has a value from about 3 to about 36 and $1 \leq n+y \leq 12$. The germanium can substitute for the silicon, zirconium or combinations thereof. Since the compositions are essentially insoluble in bodily fluids (at neutral or basic pH), they can be orally ingested in order to remove toxins in the gastrointestinal system.

In one embodiment, the composition exhibits median particle size of greater than 3 microns and less than 7% of the particles in the composition have a diameter less than 3 microns. Preferably, less than 5% of the particles in the composition have a diameter less than 3 microns, more preferably less than 4% of the particles in the composition have a diameter less than 3 microns, more preferably less than 3% of the particles in the composition have a diameter of less than 3 microns, more preferably less than 2% of the particles in the composition have a diameter of less than 3 microns, more preferably less than 1% of the particles in the composition have a diameter of less than 3 microns, more preferably less than 0.5% of the particles in the composition have a diameter of less than 3 microns. Most preferably, none of the particles or only trace amounts have a diameter of less than 3 microns.

The median and average particle size is preferably greater than 3 microns and particles reaching a sizes on the order of 1,000 microns are possible for certain applications. Preferably, the median particle size ranges from 5 to 1000 microns, more preferably 10 to 600 microns, more preferably from 15 to 200 microns, and most preferably from 20 to 100 microns.

In one embodiment, the composition exhibiting the median particle size and fraction of particles in the composition having a diameter less than 3 micron described above also exhibits a sodium content of below 12% by weight. Preferably, the sodium contents is below 9% by weight, more preferably the sodium content is below 6% by weight, more preferably the sodium content is below 3% by weight, more preferably the sodium content is in a range of between 0.05 to 3% by weight, and most preferably 0.01% or less by weight or as low as possible.

In one embodiment, the invention involves a pharmaceutical product comprising the composition in capsule or tablet form.

In one embodiment, a molecular sieve is provided which has an elevated cation exchange capacity, particularly potassium exchange capacity. The elevated cation exchange capacity is achieved by a specialized process and reactor configuration that lifts and more thoroughly suspends crystals throughout the reaction. In an embodiment of the invention, the UZSi-9 crystals had a potassium exchange capacity of greater than 2.5 meq/g, more preferably greater than 3.5 meq/g, more preferably greater than 4.0 meq/g, more preferably between 4.3 and 4.8 meq/g, even more preferably between 4.4 and 4.7 meq/g, and most preferably approximately 4.5 meq/g. UZSi-9 crystals having a potassium exchange capacity in the range of 3.7-3.9 were produced in accordance with Example 13 below.

The compositions of the present invention may be used in the treatment of hyperkalemia comprising administering the composition to a patient in need thereof. The administered dose may vary, depending on whether the treatment is for chronic or acute hyperkalemia. The dose for treating acute hyperkalemia is higher than that for the treatment of chronic hyperkalemia. For the treatment of acute hyperkalemia, the dose preferably ranges from approximately 0.7 to 1,500 mg/Kg/day, more preferably from approximately 500 to 1,000 mg/Kg/day, and most preferably approximately 700 mg/Kg/day. A typical daily dose for treatment of acute hyperkalemia, depending on the potassium exchange capacity, in a human patient will range from approximately 50 mg to 60 g per day, more preferably from approximately 1 mg to 30 g per day, more preferably 3 to 9 g per day, and most preferably approximately 3 g per day. For the treatment of chronic hyperkalemia, the dose preferably ranges from 0.25 to 100 mg/Kg/day, more preferably from 10 to 70 mg/Kg/day, and most preferably approximately 50 mg/Kg/day. A typical daily dose for treatment of chronic hyperkalemia in a human patient will range from approximately 0.020 to 10 g per day, more preferably from 0.1 to 1 g per day, and most preferably approximately 0.5 g per day.

For higher KEC compositions, the dosages will typically be lower due to the increased effectiveness of the compositions for lowering potassium levels in a patient. For the treatment of acute hyperkalemia, the dose preferably ranges from approximately 0.7 to 800 mg/Kg/day, more preferably from approximately 280 to 500 mg/Kg/day, and most preferably approximately 390 mg/Kg/day. A typical daily dose for treatment of acute hyperkalemia, depending on the potassium exchange capacity, in a human patient will range from approximately 50 mg to 33 g per day, more preferably from approximately 1 mg to 30 g per day, more preferably 3 to 9 g per day, and most preferably approximately 3 g per day. For the treatment of chronic hyperkalemia, the dose preferably ranges from 0.25 to 55 mg/Kg/day, more preferably from 5 to 40 mg/Kg/day, and most preferably approximately 30 mg/Kg/day. A typical daily dose for treatment of chronic hyperkalemia in a human patient will range from approximately 0.020 to 5 g per day, more preferably from 0.05 to 0.7 g per day, and most preferably approximately 0.5 g per day.

Compositions of the invention may be prepared by subjecting a zirconium silicate composition as described above to screening or a combination of screening and ion exchange processes as further described herein.

BRIEF DESCRIPTION OF THE DRAWINGS

FIG. 2 shows particle size distribution of ZS-9 lot 5332-04310-A in accordance with Example 8.

FIG. 3 shows particle size distribution of ZS-9 lot 5332-15410-A in accordance with Example 8.

FIG. 4 shows particle size distribution of ZS-9 preclinical lot in accordance with Example 8.

FIG. 5 shows particle size distribution of lot 5332-04310A w/o screening in accordance with Example 9.

FIG. 6 shows particle size distribution of lot 5332-04310A 635 mesh in accordance with Example 9.

FIG. 7 shows particle size distribution of lot 5332-04310A 450 mesh in accordance with Example 9.

FIG. 8 shows particle size distribution of lot 5332-04310A 325 mesh in accordance with Example 9.

FIG. 9 shows particle size distribution of lot 5332-04310A 230 mesh in accordance with Example 9.

FIG. 10: XRD plot for ZS-9 prepared in accordance with Example 12.

FIG. 11: FTIR plot for ZS-9 prepared in accordance with Example 12.

FIG. 12: XRD plot for ZS-9 prepared in accordance with Example 13.

FIG. 13: FTIR plot for ZS-9 prepared in accordance with Example 13.

FIG. 14: Example of the Blank Solution Chromatogram

FIG. 15: Example of the Assay Standard Solution Chromatogram.

FIG. 16: Exemplary Sample Chromatogram.

FIG. 17: Reaction vessel with standard agitator arrangement.

FIG. 18: Reaction vessel with baffles for production of enhanced ZS-9

FIG. 19: Detail of baffle design for 200-L reaction vessel for production of enhanced ZS-9

DETAILED DESCRIPTION OF THE INVENTION

Figure 1:
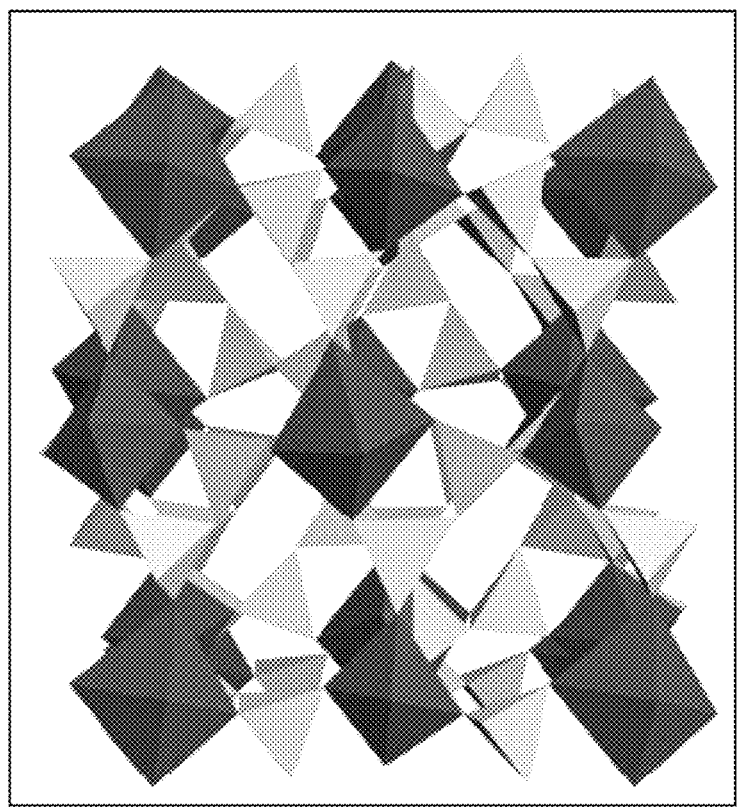
FIG. 1 is a polyhedral drawing showing the structure of microporous zirconium silicate $Na_{2.19}ZrSi_{3.01}O_{9.11} \cdot 2.71H_2O$ (MW 420.71)

The inventors have discovered novel zirconium silicate molecular sieve absorbers that address problems of adverse effects in the therapeutic use of molecular sieve absorbers, e.g., for the treatment of hyperkalemia. Zirconium silicate has a microporous framework structure composed of $ZrO_2$ octahedral units and $SiO_2$ tetrahedral units. FIG. 1 is a polyhedral drawing showing the structure of microporous zirconium silicate $Na_{2.19}ZrSi_{3.01}O_{9.11} \cdot 2.71H_2O$ (MW 420.71) The dark polygons depict the octahedral zirconium oxide units while the light polygons depict the tetrahedral silicon dioxide units. Cations are not depicted in FIG. 1.

The microporous exchanger of the invention has a large capacity and strong affinity, i.e., selectivity, for potassium or ammonium. Eleven types of zirconium silicate are available, UZSi-1 through UZSi-11, each having various affinities to ions have been developed. See e.g., U.S. Pat. No. 5,891,417. UZSi-9 (otherwise known as ZS-9) is a particularly effective zirconium silicate absorber for absorbing potassium and ammonium. These zirconium silicates have the empirical formula:

$$A_pM_xZr_{1-x}Si_nGe_yO_m \quad (I)$$

where A is an exchangeable cation selected from potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), "p" has a value from about 1 to about 20, "x" has a value from 0 to less than 1, "n" has a value from about 0 to about 12, "y" has a value from 0 to about 12, "m" has a value from about 3 to about 36 and $1 \leq n+y \leq 12$. The germanium can substitute for the silicon, zirconium or combinations thereof. It is preferred that x and y are zero or both approaching zero, as germanium and other metals are often present in trace quantities. Since the compositions are essentially insoluble in bodily fluids (at neutral or basic pH), they can be orally ingested in order to remove toxins in the gastrointestinal system.

The zirconium metallates are prepared by a hydrothermal crystallization of a reaction mixture prepared by combining a reactive source of zirconium, silicon and/or germanium, optionally one or more M metal, at least one alkali metal and water. The alkali metal acts as a templating agent. Any zirconium compound, which can be hydrolyzed to zirconium oxide or zirconium hydroxide, can be used. Specific examples of these compounds include zirconium alkoxide, e.g., zirconium n-propoxide, zirconium hydroxide, zirconium acetate, zirconium oxychloride, zirconium chloride, zirconium phosphate and zirconium oxynitrate. The sources of silica include colloidal silica, fumed silica and sodium silicate. The sources of germanium include germanium oxide, germanium alkoxides and germanium tetrachloride. Alkali sources include potassium hydroxide, sodium hydroxide, rubidium hydroxide, cesium hydroxide, sodium carbonate, potassium carbonate, rubidium carbonate, cesium carbonate, sodium halide, potassium halide, rubidium halide, cesium halide, sodium ethylenediamine tetraacetic acid (EDTA), potassium EDTA, rubidium EDTA, and cesium EDTA. The M metals sources include the M metal oxides, alkoxides, halide salts, acetate salts, nitrate salts and sulfate salts. Specific examples of the M metal sources include, but are not limited to titanium alkoxides, titanium tetrachloride, titanium trichloride, titanium dioxide, tin tetrachloride, tin isopropoxide, niobium isopropoxide, hydrous niobium oxide, hafnium isopropoxide, hafnium chloride, hafnium oxychloride, cerium chloride, cerium oxide and cerium sulfate.

Generally, the hydrothermal process used to prepare the zirconium metallate or titanium metallate ion exchange compositions of this invention involves forming a reaction mixture which in terms of molar ratios of the oxides is expressed by the formulae:

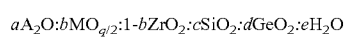

$$aA_2O : bMO_{q/2} : 1-bZrO_2 : cSiO_2 : dGeO_2 : eH_2O$$

where "a" has a value from about 0.25 to about 40, "b" has a value from about 0 to about 1, "q" is the valence of M, "c" has a value from about 0.5 to about 30, "d" has a value from about 0 to about 30 and "e" has a value of 10 to about 3000. The reaction mixture is prepared by mixing the desired sources of zirconium, silicon and optionally germanium, alkali metal and optional M metal in any order to give the desired mixture. It is also necessary that the mixture have a basic pH and preferably a pH of at least 8. The basicity of the mixture is controlled by adding excess alkali hydroxide and/or basic compounds of the other constituents of the mixture. Having formed the reaction mixture, it is next reacted at a temperature of about 100° C. to about 250° C. for a period of about 1 to about 30 days in a sealed reaction vessel under autogenous pressure. After the allotted time, the mixture is filtered to isolate the solid product which is washed with deionized water, acid or dilute acid and dried. Numerous drying techniques can be utilized including vacuum drying, tray drying, fluidized bed drying. For example, the filtered material may be oven dried in air under vacuum.

To allow for ready reference, the different structure types of the zirconium silicate molecular sieves and zirconium germanate molecular sieves have been given arbitrary designations of UZSi-1 where the "1" represents a framework of structure type "1". That is, one or more zirconium silicate and/or zirconium germanate molecular sieves with different empirical formulas can have the same structure type.

The X-ray patterns presented in the following examples were obtained using standard X-ray powder diffraction techniques and reported in U.S. Pat. No. 5,891,417. The radiation source was a high-intensity X-ray tube operated at 45 Kv and 35 ma. The diffraction pattern from the copper K-alpha radiation was obtained by appropriate computer based techniques. Flat compressed powder samples were continuously scanned at 2° (2θ) per minute. Interplanar spacings (d) in Angstrom units were obtained from the position of the diffraction peaks expressed as 2θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art, the determination of the parameter 2θ is subject to both human and mechanical error, which in combination can impose an uncertainty of about ±0.4 on each reported value of 2θ. This uncertainty is, of course, also manifested in the reported values of the d-spacings, which are calculated from the θ values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m and w which represent very strong, strong, medium, and weak, respectively. In terms of 100×$I/I_o$, the above designations are defined as w=0-15; m=15-60; s=60-80 and vs=80-100.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The crystalline compositions of the instant invention may be characterized by their X-ray powder diffraction patterns and such may have one of the X-ray patterns containing the d-spacings and intensities set forth in the following Tables. The x-ray pattern for ZS-11 as reported in U.S. Pat. No. 5,891,417, is as follows:

TABLE 1

| UZSi-11 | |
|---|---|
| d(Å) | I |
| 6.0-6.8 | w-m |
| 5.5-6.3 | m |
| 5.4-6.2 | vs |

TABLE 1-continued

| UZSi-11 | |
|---|---|
| d(Å) | I |
| 5.2-6.0 | m |
| 2.7-3.5 | s |
| 2.5-3.3 | m |

The x-ray diffraction pattern for the high-purity, high KEC ZS-9 as made in accordance with Example 13 herein (XRD shown in FIG. 13), had the following characteristics d-spacing ranges and intensities:

TABLE 2

| UZSi-9 | |
|---|---|
| d(Å) | I |
| 5.9-6.7 | m |
| 5.3-6.1 | m-s |
| 2.7-3.5 | vs |
| 2.0-2.8 | w-m |
| 1.6-2.4 | w |

The formation of zirconium silicate involves the reaction of sodium silicate and zirconium acetate in the presence of sodium hydroxide and water. The reaction has typically been conducted in small reaction vessels on the order of 1-5 Gallons. The smaller reaction vessels have been used to produce various crystalline forms of zirconium silicate including ZS-9. The inventors recognized that the ZS-9 being produced in these smaller reactors had an inadequate or undesirably low cation exchange capacity (CEC).

The inventors have discovered that the use and proper positioning of a baffle-like structure in relation to the agitator within the crystallization vessel produces a UZSi-9 crystal product exhibiting crystalline purity (as shown by XRD and FTIR spectra) and an unexpectedly high potassium exchange capacity. In smaller scale reactors (5-gal), cooling coils were positioned within the reactor to provide a baffle-like structure. The cooling coils were not used for heat exchange. Several types of cooling coils are available and the different designs may have some effect on the results presented herein, but the inventors used serpentine-type coils which snake along the inside wall of the reactor vessel.

The inventors found that the crystallization reaction used to produce UZSi-9 particularly benefited from baffles that when they are properly positioned relative to the agitator. The inventors initially produced UZSi-9 with significant levels of undesirable UZSi-11 impurity. See FIGS. 10-11. This incomplete reaction is believed to have resulted from significant amounts of solids remaining near the bottom of the reaction vessel. These solids near the bottom of the vessel remain even with conventional agitation. When properly positioned, the baffles and agitator improved the reaction conditions by creating forces within the reactor that lift the crystals within the vessel allowing for the necessary heat transfer and agitation to make a high purity form of UZSi-9. FIGS. 11-12 show XRD and FTIR spectra of high purity UZSi-9 crystals. As shown in Table 3 below, these crystals exhibit significantly higher levels of potassium exchange capacity (KEC) than the less pure ZS-9 compositions. In an embodiment of the invention, the UZSi-9 crystals had a potassium exchange capacity of greater than 2.5 meq/g, more preferably greater than 3.5 meq/g, more preferably greater than 4.0 meq/g, more preferably between 4.3 and 4.8 meq/g, even more preferably between 4.4 and 4.7 meq/g, and most preferably approximately 4.5 meq/g. UZSi-9 crystals having a potassium exchange capacity in the range of 3.7-3.9 were produced in accordance with Example 13 below.

Another unexpected benefit that came from using the reactor having a standard agitator in combination with baffles is that the high crystalline purity, high potassium exchange capacity ZS-9 crystals could be produced without utilizing any seed crystals. Prior attempts at making homogenous crystals having high crystalline purity of a single crystalline form have utilized seed crystals. The ability to eliminate the use of seed crystals was therefore an unexpected improvement relative to prior art processes.

As stated the microporous compositions of this invention have a framework structure of octahedral $ZrO_3$ units, at least one of tetrahedral $SiO_2$ units and tetrahedral $GeO_2$ units, and optionally octahedral $MO_3$ units. This framework results in a microporous structure having an intracrystalline pore system with uniform pore diameters, i.e., the pore sizes are crystallographically regular. The diameter of the pores can vary considerably from about 3 angstroms and larger.

As synthesized, the microporous compositions of this invention will contain some of the alkali metal templating agent in the pores. These metals are described as exchangeable cations, meaning that they can be exchanged with other (secondary) A' cations. Generally, the A exchangeable cations can be exchanged with A' cations selected from other alkali metal cations ($K^+$, $Na^+$, $Rb^+$, $Cs^+$), alkaline earth cations ($Mg^{2+}$, $Ca^{2+}$, $Sr^{2+}$, $Ba^{2+}$), hydronium ion or mixtures thereof. It is understood that the A' cation is different from the A cation. The methods used to exchange one cation for another are well known in the art and involve contacting the microporous compositions with a solution containing the desired cation (usually at molar excess) at exchange conditions. Typically, exchange conditions include a temperature of about 25° C. to about 100° C. and a time of about 20 minutes to about 2 hours. The use of water to exchange ions to replace sodium ions with hydronium ions may require more time, on the order of eight to ten hours. The particular cation (or mixture thereof) which is present in the final product will depend on the particular use and the specific composition being used. One particular composition is an ion exchanger where the N cation is a mixture of $Na^+$ $Ca^{+2}$ and $H^+$ ions.

When ZS-9 is formed according to these processes, it can be recovered in the Na—ZS-9 form. The sodium content of Na—ZS-9 is approximately 12 to 13% by weight when the manufacturing process is carried out at pH greater than 9. The Na—ZS-9 is unstable in concentrations of hydrochloric acid (HCl) exceeding 0.2 M at room temperature, and will undergo structural collapse after overnight exposure. While ZS-9 is slightly stable in 0.2 M HCl at room temperature, at 37° C. the material rapidly loses crystallinity. At room temperature, Na—ZS-9 is stable in solutions of 0.1M HCl and/or a pH of between approximately 6 to 7. Under these conditions, the Na level is decreased from 13% to 2% upon overnight treatment.

The conversion of Na—ZS-9 to H—ZS-9 may be accomplished through a combination of water washing and ion exchange processes, i.e., ion exchange using a dilute strong acid, e.g., 0.1 M HCl or by washing with water. Washing with water will decrease the pH and protonate a significant fraction of the zirconium silicate, thereby lowering the weight fraction of Na in the zirconium silicate. It may be desirable to perform an initial ion exchange in strong acid using higher concentrations, so long as the protonation of the zirconium silicate will effectively keep the pH from dropping to levels at which the zirconium silicate decomposes. Additional ion exchange may be accomplished with washing in water or dilute acids to further reduce the level of sodium in the zirconium silicate. The zirconium silicate made in accordance with the present invention exhibits a sodium content of below 12% by weight. Preferably, the sodium contents is below 9% by weight, more preferably the sodium content is below 6% by weight, more preferably the sodium content is below 3% by weight, more preferably the sodium content is in a range of between 0.05 to 3% by weight, and most preferably 0.01% or less by weight or as low as possible.

The ion exchanger in the sodium form, e.g., Na—ZS-9, is effective at removing excess potassium ions from a patient's gastrointestinal tract in the treatment of hyperkalemia. When the sodium form is administered to a patient, hydronium ions replace sodium ions on the exchanger leading to an unwanted rise in pH in the patient's stomach and gastrointestinal tract. Through in vitro tests it takes approximately twenty minutes in acid to stabilize sodium ion exchanger.

The hydronium form typically has equivalent efficacy as the sodium form for removing potassium ions in vivo while avoiding some of the disadvantages of the sodium form related to pH changes in the patient's body. For example, the hydrogenated form has the advantage of avoiding excessive release of sodium in the body upon administration. This can mitigate edema resulting from excessive sodium levels, particularly when used to treat acute conditions. Further, patient who are administered the hydronium form to treat chronic conditions will benefit from the lower sodium levels, particularly patients at risk for congestive heart failure. Further, it is believed that the hydronium form will have the effect of avoiding an undesirable increase of pH in the patient's urine.

The ZS-9 crystals have a broad particle size distribution. It has been theorized that small particles, less than 3 microns in diameter, could potentially be absorbed into a patient's bloodstream resulting in undesirable effects such as the accumulation of particles in the urinary tract of the patient, and particularly in the patent's kidneys. The commercially available zirconium silicates are manufactured in a way that some of the particles below 1 micron are filtered out. However, it has been found that small particles are retained in the filter cake and that elimination of particles having a diameter less than 3 microns requires the use of additional screening techniques.

The inventors have found that screening can be used to remove particles having a diameter below 3 microns and that removal of such particles is beneficial for therapeutic products containing the zirconium silicate compositions of the invention. Many techniques for particle screening can be used to accomplish the objectives of the invention, including hand screening, air jet screening, sifting or filtering, floating or any other known means of particle classification. Zirconium silicate compositions that have been subject to screening techniques exhibit a desired particle size distribution that avoids potential complications involving the therapeutic use of zirconium silicate. In general, the size distribution of particles is not critical, so long as excessively small particles are removed. The zirconium silicate compositions of the invention exhibit a median particle size greater than 3 microns, and less than 7% of the particles in the composition have a diameter less than 3 microns. Preferably, less than 5% of the particles in the composition have a diameter less than 3 microns, more preferably less than 4% of the particles in the composition have a diameter less than 3 microns, more preferably less than 3% of the particles in the composition have a diameter of less than 3 microns, more preferably less than 2% of the particles in the composition have a diameter of less than 3 microns, more preferably less than 1% of the particles in the composition have a diameter of less than 3 microns, more preferably less than 0.5% of the particles in the composition have a diameter of less than 3 microns. Most preferably, none of the particles or only trace amounts have a diameter of less than 3 microns. The median particle size is preferably greater than 3 microns and particles reaching a sizes on the order of 1,000 microns are possible for certain applications. Preferably, the median particle size ranges from 5 to 1000 microns, more preferably 10 to 600 microns, more preferably from 15 to 200 microns, and most preferably from 20 to 100 microns.

The particle screening can be conducted before, during, or after an ion exchange process such as described above whereby the sodium content of the zirconium silicate material is lowered below 12%. The lowering of sodium content to below 3% can occur over several steps in conjunction with screening or can occur entirely before or after the screening step. Particles having a sodium content below 3% may be effective with or without screening of particles sizes as described herein.

In addition to screening or sieving, the desired particle size distribution may be achieved using a granulation or other agglomeration technique for producing appropriately sized particles.

It is also within the scope of the invention that these microporous ion exchange compositions can be used in powder form or can be formed into various shapes by means well known in the art. Examples of these various shapes include pills, extrudates, spheres, pellets and irregularly shaped particles.

As stated, these compositions have particular utility in adsorbing various toxins from fluids selected from bodily fluids, dialysate solutions, and mixtures thereof. As used herein, bodily fluids will include but not be limited to blood and gastrointestinal fluids. Also by bodily is meant any mammalian body including but not limited to humans, cows, pigs, sheep, monkeys, gorillas, horses, dogs, etc. The instant process is particularly suited for removing toxins from a human body.

The zirconium metallates can also be formed into pills or other shapes which can be ingested orally and pickup toxins in the gastrointestinal fluid as the ion exchanger transits through the intestines and is finally excreted. In order to protect the ion exchangers from the high acid content in the stomach, the shaped articles may be coated with various coatings which will not dissolve in the stomach, but dissolve in the intestines.

As has also been stated, although the instant compositions are synthesized with a variety of exchangeable cations ("A"), it is preferred to exchange the cation with secondary cations (A') which are more compatible with blood or do not adversely affect the blood. For this reason, preferred cations are sodium, calcium, hydronium and magnesium. Preferred compositions are those containing sodium and calcium or sodium, calcium and hydronium ions. The relative amount of sodium and calcium can vary considerably and depends on the microporous composition and the concentration of these ions in the blood. As discussed above, when sodium is the exchangeable cation, it is desirable to replace the sodium ions with hydronium ions thereby reducing the sodium content of the composition.

The compositions of the present invention may be used in the treatment of hyperkalemia comprising administering the composition to a patient in need thereof. The administered dose may vary, depending on whether the treatment is for chronic or acute hyperkalemia. The dose for treating acute hyperkalemia is higher than that for the treatment of chronic hyperkalemia. For the treatment of acute hyperkalemia, the dose preferably ranges from approximately 0.7 to 1,500 mg/Kg/day, more preferably from approximately 500 to 1,000 mg/Kg/day, and most preferably approximately 700 mg/Kg/day. A typical daily dose for treatment of acute hyperkalemia, depending on the potassium exchange capacity, in a human patient will range from approximately 50 mg to 60 g per day, more preferably from approximately 1 mg to 30 g per day, more preferably 3 to 9 g per day, and most preferably approximately 3 g per day. For the treatment of chronic hyperkalemia, the dose preferably ranges from 0.25 to 100 mg/Kg/day, more preferably from 10 to 70 mg/Kg/day, and most preferably approximately 50 mg/Kg/day. A typical daily dose for treatment of chronic hyperkalemia in a human patient will range from approximately 0.020 to 10 g per day, more preferably from 0.1 to 1 g per day, and most preferably approximately 0.5 g per day.

For higher KEC compositions, the dosages will typically be lower due to the increased effectiveness of the compositions for lowering potassium levels in a patient. For the treatment of acute hyperkalemia, the dose preferably ranges from approximately 0.7 to 800 mg/Kg/day, more preferably from approximately 280 to 500 mg/Kg/day, and most preferably approximately 390 mg/Kg/day. A typical daily dose for treatment of acute hyperkalemia, depending on the potassium exchange capacity, in a human patient will range from approximately 50 mg to 33 g per day, more preferably from approximately 1 mg to 30 g per day, more preferably 3 to 9 g per day, and most preferably approximately 3 g per day. For the treatment of chronic hyperkalemia, the dose preferably ranges from 0.25 to 55 mg/Kg/day, more preferably from 5 to 40 mg/Kg/day, and most preferably approximately 30 mg/Kg/day. A typical daily dose for treatment of chronic hyperkalemia in a human patient will range from approximately 0.020 to 5 g per day, more preferably from 0.05 to 0.7 g per day, and most preferably approximately 0.5 g per day.

In order to more fully illustrate the invention, the following examples are set forth. It is to be understood that the examples are only by way of illustration and are not intended as an undue limitation on the broad scope of the invention as set forth in the appended claims.

Example 1

A solution was prepared by mixing 2058 g of colloidal silica (DuPont Corp. identified as Ludox™ AS-40), 2210 g of KOH in 7655 g $H_2O$. After several minutes of vigorous stirring 1471 g of a zirconium acetate solution (22.1 wt. % $ZrO_2$) were added. This mixture was stirred for an additional 3 minutes and the resulting gel was transferred to a stainless steel reactor and hydrothermally reacted for 36 hours at 200° C. The reactor was cooled to room temperature and the mixture was vacuum filtered to isolate solids which were washed with deionized water and dried in air.

The solid reaction product was analyzed and found to contain 21.2 wt. % Si, 21.5 wt. % Zr, K 20.9 wt. % K, loss on ignition (LOI) 12.8 wt. %, which gave a formula of $K_{2.3}ZrSi_{3.2}O_{9.5}*3.7H_2O$. This product was identified as sample A.

Example 2

A solution was prepared by mixing 121.5 g of colloidal silica (DuPont Corp. identified as Ludox® AS-40), 83.7 g of NaOH in 1051 g H$_2$O. After several minutes of vigorous stirring 66.9 g zirconium acetate solution (22.1 wt. % ZrO$_2$) was added. This was stirred for an additional 3 minutes and the resulting gel was transferred to a stainless steel reactor and hydrothermally reacted with stirring for 72 hours at 200° C. The reactor was cooled to room temperature and the mixture was vacuum filtered to isolate solids which were washed with deionized water and dried in air.

The solid reaction product was analyzed and found to contain 22.7 wt. % Si, 24.8 wt. % Zr, 12.8 wt. % Na, LOI 13.7 wt. %, which gives a formula Na$_{2.0}$ZrSi$_{3.0}$O$_{9.0}$*3.5H$_2$O. This product was identified as sample B.

Example 3

A solution (60.08 g) of colloidal silica (DuPont Corp. identified as Ludox® AS-40) was slowly added over a period of 15 minutes to a stirring solution of 64.52 g of KOH dissolved in 224 g deionized H$_2$O. This was followed by the addition of 45.61 g zirconium acetate (Aldrich 15-16 wt. % Zr, in dilute acetic acid). When this addition was complete, 4.75 g hydrous Nb$_2$O$_5$ (30 wt. % LOI) was added and stirred for an additional 5 minutes. The resulting gel was transferred to a stirred autoclave reactor and hydrothermally treated for 1 day at 200° C. After this time, the reactor was cooled to room temperature, the mixture was vacuum filtered, the solid washed with deionized water and dried in air.

The solid reaction product was analyzed and found to contain 20.3 wt. % Si, 15.6 wt. % Zr, 20.2 wt. % K, 6.60 wt. % Nb, LOI 9.32 wt. %, which give a formula of K$_{2.14}$Zr$_{0.71}$Nb$_{0.29}$Si$_3$O$_{9.2}$*2.32H$_2$O. Scanning Electron (SEM) of a portion of the sample, including EDAX of a crystal, indicated the presence of niobium, zirconium, and silicon framework elements. This product was identified as sample C.

Example 4

To a solution prepared by mixing 141.9 g of NaOH pellets in 774.5 g of water, there were added 303.8 g of sodium silicate with stirring. To this mixture there were added dropwise, 179.9 g of zirconium acetate (15% Zr in a 10% acetic acid solution). After thorough blending, the mixture was transferred to a Hastalloy™ reactor and heated to 200° C. under autogenous pressure with stirring for 72 hours. At the end of the reaction time, the mixture was cooled to room temperature, filtered and the solid product was washed with a 0.001 M NaOH solution and then dried at 100° C. for 16 hours. Analysis by x-ray powder diffraction showed that the product was pure ZS-11.

Example 5

To a container there was added a solution of 37.6 g NaOH pellets dissolved in 848.5 g water and to this solution there were added 322.8 g of sodium silicate with mixing. To this mixture there were added dropwise 191.2 g of zirconium acetate (15% Zr in 10% acetic acid). After thorough blending, the mixture was transferred to a Hastalloy™ reactor and the reactor was heated to 200° C. under autogenous conditions with stirring for 72 hours. Upon cooling, the product was filtered, washed with 0.001 M NaOH solution and then dried at 100° C. for 16 hours. X-ray powder diffraction analysis showed the product to be ZS-9.

Example 6

Approximately 57 g (non-volatile-free basis, lot 0063-58-30) of Na—ZS-9 was suspended in about 25 mL of water. A solution of 0.1N HCl was added gradually, with gentle stirring, and pH monitored with a pH meter. A total of about 178 milliliters of 0.1 N HCl was added with stirring, the mixture filtered then further rinsed with additional 1.2 liters 0.1 N HCl washes. The material was filtered, dried and washed with DI water. The pH of the resulting material was 7.0. The H—ZS-9 powder resulting from this three batch-wise ion exchange with 0.1 N HCl has <12% Na.

As illustrated in this example, batch-wise ion exchange with a dilute strong acid is capable of reducing the sodium content of a NA-ZS-9 composition to within a desired range.

Example 7

Approximately 85 gram (non-volatile-free basis, lot 0063-59-26) of Na—ZS-9 was washed with approximately 31 Liters of DI water at 2 Liter increments over 3 days until the pH of the rinsate reached 7. The material was filtered, dried and washed with DI water. The pH of the resulting material was 7. The H—ZS-9 powder resulting from batch-wise ion exchange and water wash has <12% Na.

As illustrated in this example, water washing is capable of reducing the sodium content of a NA-ZS-9 composition to within a desired range.

Example 8

Separate batches of ZS-9 crystals were analyzed using light scatter diffraction techniques. The particle size distribution and other measured parameters are shown in FIGS. 2-4. The d(0.1), d(0.5), and d(0.9) values represent the 10%, 50%, and 90% size values. The cumulative particle size distribution is shown in FIG. 4-6. As can be seen from the following figures, the cumulative volume of particles having a diameter below 3 microns ranges from approximately 0.3% to approximately 6%. In addition, different batches of ZS-9 have different particle size distributions with varying levels of particles having a diameter of less than 3 microns.

Example 9

Crystals of ZS-9 were subject to screening to remove small diameter particles. The resulting particle size distribution of the ZS-9 crystals screened using different size screens was analyzed. As illustrated in the following figures, the fraction of particles having a diameter below 3 microns can be lowered and eliminated using an appropriate mesh size screen. Without screening, approximately 2.5% percent of the particles had a diameter of below 3 microns. See FIG. 5. Upon screening with a 635 mesh screen, the fraction of particles having a diameter below 3 microns was reduced to approximately 2.4%. See FIG. 6. Upon screening with a 450 mesh screen, the fraction of particles having a diameter below 3 microns was reduced further to approximately 2%. See FIG. 7. When a 325 mesh screen is used, the fraction of particles having a diameter below 3 microns is further reduced to approximately 0.14%. See FIG. 8. Finally, a 230 mesh screen reduces the fraction of particles below 3 microns to 0%. See FIG. 9.

The screening techniques presented in this example illustrate that particle size distributions may be obtained for ZS-9 that provide little or no particles below 3 microns. It will be appreciated that ZS-9 according to Example 5 or H—ZS-9 according to Examples 6 and 7 may be screened as taught in this example to provide a desired particle size distribution. Specifically, the preferred particle size distributions disclosed herein may be obtained using the techniques in this example for both ZS-9 and H—ZS-9.

Example 10

A 14-Day repeat dose oral toxicity study in Beagle Dogs with Recovery was conducted. This GLP compliant oral toxicity study was performed in beagle dogs to evaluate the potential oral toxicity of ZS-9 when administered at 6 h intervals over a 12 h period, three times a day, in food, for at least 14 consecutive days. In the Main Study ZS-9 was administered to 3/dogs/sex/dose at dosages of 0 (control), 325, 650 or 1300 mg/kg/dose. An additional 2 dogs/sex/dose, assigned to the Recovery Study, received 0 or 1300 mg/kg/dose concurrently with the Main study animals and were retained off treatment for an additional 10 days. A correction factor of 1.1274 was used to correct ZS-9 for water content. Dose records were used to confirm the accuracy of dose administration.

During the acclimation period (Day −7 to Day −1) dogs were trained to eat 3 portions of wet dog chow at 6 h intervals. During treatment the requisite amount of test article (based on the most recently recorded body weight) was mixed with ~100 g of wet dog food and offered to the dogs at 6 h intervals. Additional dry food was offered following consumption of the last daily dose. Each dog received the same amount of wet dog feed. Body weights were recorded at arrival and on Days −2, −1, 6, 13 and 20. Clinical observations were performed twice daily during the acclimation, treatment and recovery periods. Wet and dry food consumption was measured daily during the treatment period. Blood and urine samples for analysis of serum chemistry, hematology, coagulation and urinalysis parameters were collected pretest (Day −1) and Day 13. Ophthalmologic examinations were performed pretest (Day −6/7) and on Day 7 (females) or 8 (males). Electrocardiographic assessments were performed pretest (Day −1) and on Day 11. At study termination (Day 14—Main Study and Day 24—Recovery Study), necropsy examinations were performed, protocol specified organ weights were weighed, and selected tissues were microscopically examined.

Oral administration of 325, 650 and 1300 mg ZS-9/kg/dose with food, three times a day at 6 h intervals over a 12-hour period for 14 days was well tolerated. Clinical signs were limited to the observation of white material, presumed to be test article, in the feces of some dogs at the 325 mg/kg/dose and in all animals receiving ≥650 mg/kg/dose during the second week of treatment. There were no adverse effects on body weight, body weight change, food consumption, hematology and coagulation parameters or ophthalmoscopic and ECG evaluations.

There were no macroscopic findings associated with administration of ZS-9. Microscopically, minimal to mild focal and/or multifocal inflammation was observed in the kidneys of treated animals but not in Control animals. The lesions had similar incidence and severity at 650 and 1300 mg/kg and were less frequent and severe at 325 mg/kg. In some dogs the inflammation was unilateral rather than bilateral and in some cases was associated with inflammation in the urinary bladder and origin of the ureter. Taken together these observations suggest that factors other than direct renal injury, such as alterations in urine composition of ZS-9-treated dogs may have resulted in increased susceptibility to subclinical urinary tract infections, even though no microorganisms were observed in these tissues. In recovery animals the inflammation was completely resolved in females and partly resolved in males suggesting that whatever the cause of the inflammation it was reversible following cessation of dosing. The increased incidence of mixed leukocyte inflammation observed in Beagle dogs treated with ZS-9 is summarized below.

Summary of Inflammation in Kidneys
Terminal Necropsy (TN): Day 14

| | | 0 mg/kg | | 325 mg/kg | | 650 mg/kg | | 1,300 mg/kg | |
|---|---|---|---|---|---|---|---|---|---|
| | | \multicolumn{8}{c}{Sex} | | | | | | | |
| | | M | F | M | F | M | F | M | F |
| | | \multicolumn{8}{c}{Number of Animals} | | | | | | | |
| | | 3 | 3 | 3 | 3 | 3 | 3 | 3 | 3 |
| Left Kidney | Incidence | 0/3 | 0/3 | 0/3 | 2/3 | 2/3 | 3/3 | 3/3 | 3/3 |
| | minimal | 0/3 | 0/3 | 0/3 | 2/3 | 2/3 | 2/3 | 3/3 | 1/3 |
| | mild | 0/3 | 0/3 | 0/3 | 0/3 | 0/3 | 1/3 | 0/3 | 2/3 |
| Right Kidney | Incidence | 0/3 | 0/3 | 1/3 | 1/3 | 2/3 | 3/3 | 2/3 | 2/3 |
| | minimal | 0/3 | 0/3 | 1/3 | 1/3 | 2/3 | 1/3 | 2/3 | 0/3 |
| | mild | 0/3 | 0/3 | 0/3 | 0/3 | 0/3 | 2/3 | 0/3 | 2/3 |
| Both Kidneys | Incidence | 0/6 | 0/6 | 1/6 | 3/6 | 4/6 | 6/6 | 5/6 | 5/6 |
| | minimal | 0/6 | 0/6 | 1/6 | 3/6 | 4/6 | 3/6 | 5/6 | 1/6 |
| | mild | 0/6 | 0/6 | 0/6 | 0/6 | 0/6 | 3/6 | 0/6 | 4/6 |
| Sum of Severity Scores | | 0 | 0 | 2 | 3 | 4 | 9 | 5 | 9 |
| | | \multicolumn{2}{c}{0} | \multicolumn{2}{c}{5} | \multicolumn{2}{c}{13} | \multicolumn{2}{c}{14} | | |
| Mean Group Severity Scores | | \multicolumn{2}{c}{0.00} | \multicolumn{2}{c}{0.83} | \multicolumn{2}{c}{2.17} | \multicolumn{2}{c}{2.33} | | |

Minimal acute urinary bladder inflammation and unidentified crystals were also observed in the renal pelvis and urine of females dosed at 650 mg/kg/dose as summarized below Summary of Crystals observed at the 650 mg/kg/dose

| | Animal No | | |
|---|---|---|---|
| | 4420 | 4421 | 4422 |
| Unidentified crystals in urine | + | − | + |
| Crystals in renal pelvis | − | + | − |
| Urinary bladder acute inflammation | + | + | − |

Crystals were not identified in group 2 or 4 females or in any ZS-9 treated males.

In both studies it was noted that urinary pH was elevated compared to control and it was postulated that the change in urinary pH and/or urinary composition affected urine solute solubility resulting in crystal formation that caused urinary tract irritation and/or increased susceptibility to urinary tract infections (UTIs).

The description of the urinary crystals (long thin spiky clusters) coupled with the particle size profile and insolubility of test article make it very unlikely that these crystals are ZS-9.

Example 11

Crystals of ZS-9 are prepared and designated "ZS-9 Unscreened." Screening in accordance with the procedures of Example 10 is conducted on a sample of ZS-9 crystals and the screened sample is designated "ZS-9>5 µm." Another sample of Crystals of ZS-9 undergo an ion exchange in accordance with the procedures of Example 6 above and are then screened in accordance with the procedures of Example 10. The resulting H—ZS-9 crystals are designated "ZS-9+ >5 μm."

The following 14-day study is designed to show the effect of particle size and particle form on the urinary pH and presence of crystals in the urine. The compounds above are administered to beagles orally by mixing with wet dog food. The regimen is administered 3 times a day at 6 hour intervals over a 12 hour period in the following manner:

Study Design

| Group | mg/kg/dose* | Female |
|---|---|---|
| Control | 0 | 3 |
| ZS-9 Unscreened | 750 | 3 |
| ZS-9 >5 μm | 750 | 3 |
| ZS-9+ >5 μm | 750 | 3 |
| ZS-9 Unscreened | 100 | 3 |
| ZS-9 >5 μm | 100 | 3 |
| ZS-9+ >5 μm | 100 | 3 |
| NaHCO$_3$ | 50 | 3 |

*uncorrected for water
ZS-9+ = pH neutral crystal

| | |
|---|---|
| Total number of dogs | 24 females |
| Age | 5 months of age on arrival |
| Acclimation | ≥10 days |
| Test Article Formulation | Mixed with wet dog food |
| Test article administration | Within 30 minutes of administration |
| Dose Formulation Analysis | Dose records will be used to confirm dosing. Weight of any remaining wet food will be recorded. |

The following table outlines the observations, toxicokinetic evaluation, laboratory investigation (hematology, urinalysis), and terminal procedures.

| Observations | |
|---|---|
| Mortality & Signs of ill health or reaction to treatment | Twice daily (after treatment and evening) including feces assessment |
| Detailed Exam | During acclimation, weekly on study |
| Body Weights | Arrival, Day −1, Day 7 and 14 |
| Food Consumption | Daily (Wet and Dry food) |
| Ophthalmoloscopy | None |
| Toxicokinetic (for potential Zr analysis) | |
| 3 × 1 ml whole blood/sample with sample weights recorded | Day −1: Pre-dose |
| | Day 13: Pre-dose and 4 h post 2$^{nd}$ dose |
| Laboratory Investigations | |
| Hematology/ Clinical chemistry (see list) | Pretreatment and during Weeks 1 and 2 on study |
| Urinalysis (see list) | Pretreatment and during Weeks 1 and 2 on study (Metabolic cage, urine sample to be kept cool) Remaining urine aliquoted and retained frozen for possible future Zr analysis |
| Terminal Procedures | |
| Necropsy | All animals regardless of mode of death. All tissues collected into NBF (see list) |
| Histopathology | Urinary tract only (Kidney and bladder) |

These tests show that the zirconium silicates of the present invention are particularly suitable for the treatment of hyperkalemia.

Example 12

UZSi-9 crystals were prepared by reaction in a standard 5-G crystallization vessel.

The reactants were prepared as follows. A 22-L Morton flask was equipped with an overhead stirrer, thermocouple, and an equilibrated addition funnel. The flask was charged with deionized water (3.25 L). Stirring was initiated at approximately 100 rpm and sodium hydroxide (1091 g NaOH) was added to the flask. The flask contents exothermed as the sodium hydroxide dissolved. The solution was stirred and cooled to less than 34° C. Sodium silicate solution (5672.7 g) was added. To this solution was added zirconium acetate solution (3309.5 g) over 43 minutes. The resulting suspension was stirred for another 22 minutes. Seed crystals of ZS-9 (223.8 g) were added to the reaction vessel and stirred for approximately 17 minutes.

The mixture was transferred to a 5-G Parr pressure vessel with the aid of deionized water (0.5 L). The vessel had smooth walls and a standard agitator. The reactor did not have a cooling coil present. The vessel was sealed and the reaction mixture was stirred at approximately 275-325 rpm and heated to 185+/−10° C. over 4 hours, then held at 184-186° C. and soaked for 72 hours. Finally, the reactants were then cooled to 80° C. over 12.6 hours. The resulting white solid was filtered with the aid of deionized water (18 L). The solids were washed with deionized water (125 L) until the pH of the eluting filtrate was less than 11 (9.73). The wet cake was dried in vacuo (25 inches Hg) for 48 hours at 95-105° C. to give 2577.9 g (107.1%) of ZS-9 as a white solid.

The XRD plot of the ZS-9 obtained in this example is shown in FIG. 10. The FTIR plot of this material is shown in FIG. 11. These XRD and FTIR spectra are characterized by the presence of absorption peaks typically associated with the ZS-11 crystalline form. In addition, the peaks that are associated with ZS-9 exhibit significant spreading due to crystal impurities (e.g. the presence of ZS-11 crystals in a ZS-9 composition). For example, the FTIR spectra shows significant absorption around 764 and 955 cm$^{-1}$. The XRD plot for this example exhibits significant noise and poorly defined peaks at 2-theta values of 7.5, 32, and 42.5.

Example 13

High capacity UZSi-9 crystals were prepared in accordance with the following representative example.

The reactants were prepared as follows. A 22-L Morton flask was equipped with an overhead stirrer, thermocouple, and an equilibrated addition funnel. The flask was charged with deionized water (8,600 g, 477.37 moles). Stirring was initiated at approximately 145-150 rpm and sodium hydroxide (661.0 g, 16.53 moles NaOH, 8.26 moles Na2O) was added to the flask. The flask contents exothermed from 24° C. to 40° C. over a period of 3 minutes as the sodium hydroxide dissolved. The solution was stirred for an hour to allow the initial exotherm to subside. Sodium silicate solution (5,017 g, 22.53 mole SO2, 8.67 moles Na2O) was added. To this solution, by means of the addition funnel, was added zirconium acetate solution (2,080 g, 3.76 moles ZrO2) over 30 min. The resulting suspension was stirred for and additional 30 min.

The mixture was transferred to a 5-G Parr pressure vessel Model 4555 with the aid of deionized water (500 g, 27.75 moles). The reactor was fitted with a cooling coil having a serpentine configuration to provided a baffle-like structure within the reactor adjacent the agitator. The cooling coil was not charged with heat exchange fluid as it was being used in this reaction merely to provide a baffle-like structure adjacent the agitator.

The vessel was sealed and the reaction mixture was stirred at approximately 230-235 rprn and heated from 21° C. to 140-145° C. over 7.5 hours and held at 140-145° C. for 10.5 hours, then heated to 210-215° C. over 6.5 hours where the maximum pressure of 295-300 psi was obtained, then held at 210-215° C. for 4 1.5 hours. Subsequently, the reactor was cooled to 45° C. over a period of 4.5 hours. The resulting white solid was filtered with the aid of deionized water (1.0 KG). The solids were washed with deionized water (40 L) until the pH of the eluting filtrate was less than 11 (10.54). A representative portion of the wet cake was dried in vacuo (25 inches Hg) overnight at 100° C. to give 1,376 g (87.1%) of ZS-9 as a white solid.

The XRD plot of the ZS-9 obtained is shown in FIG. 12. The FTIR plot of this material is shown in FIG. 13. These XRD and FTIR spectra, when compared to those for Example 12 (FIGS. 10-11), exhibited well-delineated peaks without spreading and the absence of peaks associated with crystalline forms other than ZS-9 (e.g., ZS-11 peaks). This example illustrates how the presence of a baffle-like structure within the reactor drastically and unexpectedly improves the quality of the thus obtained crystals. Although not wishing to be bound by theory, the inventors understand that baffles provide added turbulence which lifts the solids (i.e., crystals) and results in a more even suspension of crystals within the reaction vessel while the reaction is ongoing. This improved suspension allows for more complete reaction to the desired crystalline form and reduces the presence of unwanted crystalline forms of zirconium silicate in the end product.

Example 14

The potassium exchange capacity (KEC) of zirconium silicate (ZS-9) was determined according to the following protocol.

This test method used a HPLC capable of gradient solvent introduction and cation exchange detection. The column was an IonPac CS12A, Analytical (2×250 mm). The flow rate was 0.5 mL/minute with a run time of approximately 8 minutes. The column temperature was set to 35° C. The injection volume was 10 μL and the needle wash was 250 μL. The pump was operated in Isocratic mode and the solvent was DI water.

A stock standard was prepared by accurately weighing and recording the weight of about 383 mg of potassium chloride (ACS grade), which was transferred into a 100-rnL plastic volumetric flask. The material was dissolved and diluted to volume with diluent followed by mixing. The stock standard had a K$^+$ concentration of 2000 ppm (2 mg/mL). Samples were prepared by accurately weighing, recording, and transferring about 112 mg of ZS-9 into a 20 mL plastic vial. 20.0 mL of the 2000 ppm potassium stock standard solution was pipetted into the vial and the container was closed. The sample vials were placed onto a wrist action shaker and were shook for at least 2 hours but not more than 4 hours. The sample preparation solution was filtered through a 0.45 pm PTFE filter into a plastic container. 750 pL of the sample solution was transferred into a 100-mL plastic volumetric flask. The sample was diluted to volume with DI water and mixed. The initial K$^+$ concentration was 15 ppm (1 SpgImL).

The samples were injected into the HPLC. FIG. 14 shows an example of the blank solution chromatogram. FIG. 15 shows an example of the assay standard solution chromatogram. FIG. 16 shows an exemplary sample chromatogram. The potassium exchange capacity was calculated using the following formula:

$$KEC = \frac{\frac{(IC - FC) \times V}{Eq\text{ wt.}}}{\text{Wt·}_{SPL} \times \frac{100\% - \%\text{ Water}}{100\%} \times \frac{1\text{ g}}{1000\text{ mg}}}$$

KEC is the potassium exchange capacity in mEq/g. The initial concentration of potassium (ppm) is IC. The final concentration of potassium (ppm) is FC. The equivalent weight (atomic weight/valence) is Eq wt. The volume (L) of standard in sample preparation is V. The weight of ZS-9 (mg) used for sample preparation is Wt$_{spl}$. The percent (%) of water content (LOD) is % water.

Three samples of ZS-9 produced in accordance with the procedures of Example 12, i.e., in a reactor without baffles (e.g., internal cooling coil structure), were tested for potassium exchange capacity (KEC) in accordance with the above-referenced procedure. Likewise, three samples of ZS-9 produced in accordance with Example 13 in a reactor having cooling coils serving as baffles were tested in accordance with this procedure. The results in Table 3 below show that the procedure of Example 13 and the presence of baffles within the crystallization vessel resulted in a dramatic increase in the potassium exchange capacity.

TABLE 3

| Potassium Exchange Capacity (KEC) | | | |
|---|---|---|---|
| Example 12 (Without baffles) | | Example 13 (With baffles) | |
| Lot 5368-10311A | 2.3 meq/gm | Lot 2724-9A | 3.9 meq/gm |
| Lot 5368-12211A | 1.7 meq/gm | Lot 2724-13D | 3.8 meq/gm |
| Lot 5368-13811A | 1.8 meq/gm | Lot 2724-18F | 3.8 meq/gm |

Example 15

The use of an internal cooling coil to provide a baffle-like structure within the reactor is only feasible for small reactors on the order of 5-gallons because larger reactors cannot be easily fitted with, and typically do not utilized, cooling coils.

The inventors have designed a reactor for larger-scale production of high purity, high-KEC ZS-9 crystals. Large-scale reactors typically utilize a jacket for achieving heat transfer to the reaction chamber rather than coils suspended within the reaction chamber. A conventional 200-L reactor 100 is shown in FIG. 17. The reactor 100 has smooth walls and an agitator 101 extending into the center of the reaction chamber. The reactor 100 also has a thermowell 102 and a bottom outlet valve 103. The inventors have designed an improved reactor 200, FIG. 18, which also has an agitator 201, thermowell 202, and bottom outlet valve 203. The improved reactor 200 has baffle structures 204 on its sidewalls, which in combination with the agitator 201 provide significant lift and suspension of the crystals during reaction and the creation of high purity, high KEC ZS-9 crystals. The improved reactor can also include a cooling or heating jacket for controlling the reaction temperature during crystallization in addition to the baffle structures 204. The details of an exemplary and non-limiting baffle design is shown in FIG.

19. Preferably the reactor has a volume of at least 20-L, more preferably 200-L or more, or within the range of 200-L to 30,000-L.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

The invention claimed is:

1. A method of removing excess potassium ions and ammonium ions comprising administering to a subject in need thereof a composition comprising a zirconium silicate particle of formula (I):

$$A_pM_xZr_{1-x}Si_nGe_yO_m \quad (I)$$

where A is a potassium ion, sodium ion, rubidium, ion, cesium ion, calcium ion, magnesium ion, hydronium ion or mixtures thereof, M is at least one framework metal, wherein the framework metal is hafnium (4+), tin (4+), niobium (5+), titanium (4+), cerium (4+), germanium (4+), praseodymium (4+), terbium (4+) or mixtures thereof, "p" has a value from about 1 to about 20, "x" has a value from 0 to less than 1, "n" has a value from about 0 to about 12, "y" has a value from 0 to about 12, "m" has a value from about 3 to about 36 and $1 \leq n+y \leq 12$, wherein the zirconium silicate particles are in a form of ZS-1, ZS-2, ZS-6, ZS-7, ZS-8, ZS-9, or ZS-11 that exhibit a uniform microporous structure and have median particle size of greater than 3 microns and less than 7% of the particles in the composition have a diameter less than 3 microns, and the composition exhibits a sodium content below 12% by weight.

2. The method of claim 1, wherein the sodium content is less than 6% by weight.

3. The method of claim 1, wherein the sodium content is between 0.05 to 3% by weight.

4. The method of claim 1, wherein the sodium content is less than 0.01% by weight.

5. The method of claim 1, wherein less than 4% of the particles in the composition have a diameter less than 3 microns.

6. The method of claim 1, wherein less than 1% of the particles in the composition have a diameter less than 3 microns.

7. The method of claim 1, wherein the median particle size ranges from 5 to 1000 microns.

8. The method of claim 1, wherein the median particle size ranges from 20 to 100 microns.

9. The method of claim 1, wherein the composition comprises a zirconium silicate in the form of ZS-9 and exhibits an x-ray powder diffraction spectrum indicating at least the following d-spacing values:
    a first d-spacing within the range of 2.7-3.5 angstroms having a first intensity value,
    a second d-spacing within the range of 5.3-6.1 having a second intensity value, wherein the second intensity value is less than the first intensity value,
    a third d-spacing within the range of 1.6-2.4 angstroms having a third intensity value,
    a fourth d-spacing within the range of 2.0-2.8 angstroms having a fourth intensity value, and
    a fifth d-spacing within the range of 5.9-6.7 angstroms having a fifth intensity value, wherein the third, fourth, and fifth intensity values are each lower than the first and second intensity values.

10. The method of claim 1, wherein the subject is suffering from hyperkalemia, hyperammonemia, or both.

11. The method of claim 10, wherein the hyperkalemia is acute hyperkalemia.

12. The method of claim 11, wherein the subject is administered a dose of approximately 0.7 to 1,500 mg/Kg/day.

13. The method of claim 11, wherein the subject is administered a dose of approximately 500 to 1,000 mg/Kg/day.

14. The method of claim 11, wherein the subject is administered a dose of approximately 700 mg/Kg/day.

15. The method of claim 10, wherein the hyperkalemia is chronic hyperkalemia.

16. The method of claim 15, wherein the subject is administered a dose of approximately 0.25 to 100 mg/Kg/day.

17. The method of claim 15, wherein the subject is administered a dose of approximately 10 to 70 mg/Kg/day.

18. The method of claim 15, wherein the subject is administered a dose of approximately 50 mg/Kg/day.

19. The method of claim 1, wherein the subject is at risk for congestive heart failure.

20. The method of claim 1, wherein the subject has edema from elevated sodium levels.

21. The method of claim 1, wherein the FTIR spectra of the composition does not include absorption peaks at approximately 764 and 955 $cm^{-1}$.

22. The method of claim 1, wherein the XRD plot of the composition does not indicate significant peaks at 2-theta values of 7.5, 32, or 42.5.

* * * * *